US006444709B1

(12) United States Patent
Diaz et al.

(10) Patent No.: US 6,444,709 B1
(45) Date of Patent: Sep. 3, 2002

(54) HETEROETHYLENE COMPOUNDS AND PHARMACEUTICAL AND COSMETIC COMPOSITIONS CONTAINING SAME

(75) Inventors: Philippe Diaz, Nice; Jean-Michel Bernardon, Le Rouret, both of (FR)

(73) Assignee: Galderma Research & Development S.N.C., Valbonne (FR)

( * ) Notice: Subject to any disclaimer, the term of this patent is extended or adjusted under 35 U.S.C. 154(b) by 0 days.

(21) Appl. No.: 09/424,816

(22) PCT Filed: Mar. 29, 1999

(86) PCT No.: PCT/FR99/00727

§ 371 (c)(1),
(2), (4) Date: Feb. 7, 2000

(87) PCT Pub. No.: WO99/50239

PCT Pub. Date: Oct. 7, 1999

(30) Foreign Application Priority Data

Mar. 31, 1998 (FR) .............................................. 98 03977

(51) Int. Cl.[7] ................... A61K 31/095; A61K 31/045; A61K 31/075; A61K 31/335; A61K 31/38; C07C 43/00; C07C 317/00; C07C 321/00; C07C 391/00

(52) U.S. Cl. ....................... 514/706; 514/430; 514/432; 514/438; 514/443; 514/449; 514/451; 514/453; 514/456; 514/461; 514/468; 514/469; 514/708; 514/709; 514/710; 514/712; 514/713; 514/715; 514/717; 514/718; 514/719; 514/720; 514/724; 514/730; 514/738; 514/739; 514/824; 514/825; 514/859; 514/861; 514/863; 514/864; 514/866; 514/880; 514/886; 514/887; 514/902; 514/909; 514/912; 549/15; 549/29; 549/41; 549/49; 549/381; 549/396; 549/456; 549/462; 562/899; 568/18; 568/25; 568/300; 568/626

(58) Field of Search .................. 514/430, 449, 514/706, 717, 708, 709, 710, 712, 713, 432, 438, 443, 451, 453, 456, 461, 468, 469, 715, 718, 719, 720, 724, 730, 738, 739, 824, 825, 859, 861, 863, 864, 866, 880, 886, 887, 902, 909, 912; 549/15, 29, 41, 49, 381, 396, 456, 462; 562/899; 568/18, 25, 300, 626

(56) References Cited

FOREIGN PATENT DOCUMENTS

EP  0 679 630  11/1995
EP  0 776 885  6/1997

OTHER PUBLICATIONS

STN/CAS online, file CAPLUS, Acc. No. 1993:625606, Doc. No. 119:225606, (Houpis et al., Synlett (1993), (5), 365–6), Abstract.*

C. Maignan et al, Bull. Soc. Chim. Fr., No. 4, 1986, pp. 645–649, XP002114593, p. 647, col. 2, composé 3a; p. 648, col. 2, composé 3YE.

Database Chemabs "Online", Chemical Abstracts Service, Columbus, Ohio, STN, Caplus, Accession No. 1981:550094, XP002114599 abrégé; RN 79354–19–1 & E.Y. Kolosov et al, ZH.ORG.KHIM., vol. 17, No. 6, 1981, pp. 1184–1190.

Database Chemabs "Online", Chemical Abstracts Service, Columbus, Ohio, STN, CAPLUS, Accession No. 1976:523496, XP002114600 abrégé; RN 60983–97–3 & L.A. Bez'yazychnaya et al, ZH. OBSHCH. KHIM., vol. 46, No. 7, 1976, pp. 1557–1566.

R.S. Paley et al, J. Org. Chem., vol. 62, No. 18, 1997, pp. 6326–6343, XP002114594, p. 6335, composé 7d; p. 6336, composés 10c, 10g; p. 6338, composés 15a, 16a.

X. Huang et al: Synthesis, No. 10, 1996, pp. 1191–1192, XP002114595, p. 1192, composé 5d.

G. Solladie et al, Synthesis, No. 11, 1991, pp. 1011–1012, XP002114596, p. 1011, composés 3a–b.

J. Barluenga et al, J. Chem. Soc. Perkin Trans 1, No. 12, 1987, pp. 2605–2609, XP002114597, p. 2606, composé 19.

M.C. Barnabeu et al, Tetrahedron Lett., vol. 36, No. 22, 1995, pp. 3901–3904, XP002114598, p. 3902, composés 1a–c.

M.C. Barnabeu et al, Tetrahedron Lett., vol. 37, No. 20, 1996, pp. 3595–3598, XP004029356.

E. Arce et al, Tetrahedron: Asymmetry, vol. 6, No. 7, 1995, pp. 1757–1764, XP004048152, p. 1759, composé 1a.

Database Chemabs "Online", Chemical Abstracts Service, Columbus, Ohio, US, STN, CAPLUS, Accession No., 1972:501313, XP002114939, abrége; RN 38276–74–3 & Chemical Abstracts, vol. 77, No. 15, Oct. 9, 1972, Columbus, Ohio, US; Abstract No. 101313z, abrégé & E. Schmid et al: Helv. Chim. Acta, vol. 55, No. 5, 1972, pp. 1625–1674.

* cited by examiner

Primary Examiner—Jose' G. Dees
Assistant Examiner—Frank Choi
(74) Attorney, Agent, or Firm—Burns, Doane, Swecker & Mathis, L.L.P.

(57) ABSTRACT

The invention relates to novel heteroethynylenic compounds having the general formula (I):

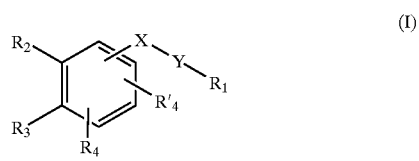

(I)

as well as to the use of these compounds in pharmaceutical compositions intended for use in human or veterinary medicine (dermatological, rheumatic, respiratory, cardiovascular and ophthalmological complaints in particular), or alternatively in cosmetic compositions.

16 Claims, No Drawings

HETEROETHYLENE COMPOUNDS AND PHARMACEUTICAL AND COSMETIC COMPOSITIONS CONTAINING SAME

This application is a 371 of PCT/FR99/00727, filed Mar. 29, 1999.

The invention relates, as novel and useful industrial products, to heteroethynylenic compounds. It also relates to the use of these novel compounds in pharmaceutical compositions intended for a use in human or veterinary medicine, or alternatively in cosmetic compositions.

The compounds according to the invention have pronounced activity in the fields of cell differentiation and proliferation, and find applications more particularly in the topical and systemic treatment of dermatological complaints associated with a keratinization disorder, dermatological (or other) complaints with an inflammatory and/or immunoallergic component, and dermal or epidermal proliferations, whether they are benign or malignant. These compounds can also be used in the treatment of degenerative diseases of connective tissue, to combat ageing of the skin, whether this is light-induced or chronological ageing, and to treat cicatrization disorders. They moreover find an application in the ophthalmological field, in particular in the treatment of corneopathies.

The compounds according to the invention can also be used in cosmetic compositions for body and hair hygiene.

The compounds according to the invention can be represented by the general formula (I) below:

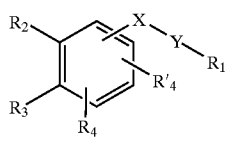

(I)

in which:

| —$R_1$ represents: | (i) a —$CH_3$ radical<br>(ii) a radical —$CH_2$—O—$R_5$<br>(iii) a radical —$COR_6$ |
|---|---|

$R_5$ and $R_6$ having the meanings given below,

X represents: O, Se, S(O)n, n being 0, 1 or 2,

Y represents a divalent radical which has the formula:

 a)

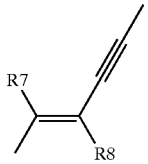 b)

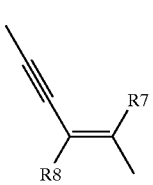 c)

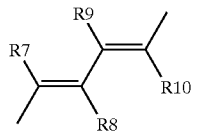 d)

$R_7$, $R_8$, $R_9$ and $R_{10}$ having the meanings given below, $R_2$ and $R_3$, taken together, form, with the adjacent aromatic ring, a 5- or 6-membered ring optionally substituted with methyl groups and/or optionally interrupted by an oxygen or sulphur atom, given that $R_2$ and $R_3$ independently, which may be identical or different, can represent:
  a) a hydrogen atom,
  b) a radical chosen from the following radicals
    methyl,
    tert-butyl,
    1-methylcyclohexyl,
    1-adamantyl,
  c) a radical —$OR_{11}$
  d) a polyether radical
  e) a halogen atom $R_{11}$ having the meaning given below, it being understood that at least one of the substituents $R_2$ and $R_3$ represents (b), $R_4$ represents a hydrogen atom, a lower alkyl radical, a radical $OR_{12}$, a polyether radical, a radical $COR_{13}$ or a halogen atom, $R_{12}$ and $R_{13}$ having the meanings given below, $R'_4$ represents a hydrogen atom or a halogen atom, $R_5$ represents a hydrogen atom or a lower alkyl radical, $R_6$ represents:
  (i) a hydrogen atom
  (ii) a lower alkyl radical
  (iii) a radical $OR_{14}$
    $R_{14}$ having the meaning given below
  (iv) a radical of formula

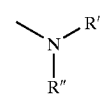

R' and R" having the meanings given below, $R_7$, $R_8$, $R_9$ and $R_{10}$, which may be identical or different, represent a hydrogen atom, a lower alkyl radical or an aryl radical, $R_{11}$ and $R_{12}$, which may be identical or different, represent a hydrogen atom, a lower alkyl radical, an optionally substituted aryl radical, an optionally substituted aralkyl radical, a monohydroxyalkyl or polyhydroxyalkyl radical or a lower acyl radical, $R_{13}$ represents a lower alkyl radical, a radical $OR_{15}$ or a radical

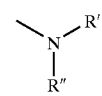

$R_{15}$, R' and R" having the meanings given below, $R_{14}$ and $R_{15}$, which may be identical or different, represent a hydrogen atom, a lower alkyl radical, an aryl radical, an optionally substituted aralkyl radical, a monohydroxyalkyl radical or a polyhydroxyalkyl radical, R' and R", which may be identical or different, represent a hydrogen atom, a lower alkyl radical, a mono- or polyhydroxyalkyl radical, an optionally substituted aryl radical or an amino acid residue, or alternatively, taken together with the nitrogen atom, form a heterocycle.

The invention is also directed towards the salts of the compounds of formula (I) when $R_1$ represents a carboxylic acid function and the geometrical and optical isomers of the said compounds of formula (I).

When the compounds according to the invention are in the form of salts, they are preferably salts of an alkali metal or alkaline earth metal, or alternatively of zinc or of an organic amine.

The term "lower alkyl radical" means a radical containing from 1 to 6 carbon atoms, and preferably methyl, ethyl, isopropyl, butyl and tert-butyl radicals.

The term "monohydroxyalkyl radical" should be understood as meaning a radical containing from 1 to 6 carbon atoms, in particular a 2-hydroxyethyl, 2-hydroxypropyl or 3-hydroxypropyl radical.

The term "polyhydroxyalkyl radical" should be understood as meaning a radical containing from 2 to 6 carbon atoms and from 2 to 5 hydroxyl groups, such as 2,3-dihydroxypropyl, 2,3,4-trihydroxybutyl or 2,3,4,5-tetrahydroxypentyl radicals or a pentaerythritol residue.

The term "optionally substituted aryl radical" should be understood as meaning a phenyl radical optionally substituted with at least one halogen atom, a hydroxyl or a nitro function.

The term "optionally substituted aralkyl radical" should be understood as meaning a benzyl or phenethyl radical optionally substituted with at least one halogen atom, a hydroxyl or a nitro function.

The term "lower acyl radical" should be understood as meaning a radical containing from 1 to 4 carbon atoms, in particular an acetyl or propionyl radical.

The term "amino acid residue" should be understood as meaning a residue derived, for example, from one of the 20 amino acids of L or D configuration which constitute mammalian proteins.

The term "heterocycle" preferably means a piperidino, morpholino, pyrrolidino or piperazino radical, optionally substituted in position 4 with a $C_1$–$C_6$ alkyl or mono- or polyhydroxyalkyl radical as defined above.

The term "polyether radical" means a radical containing from 1 to 6 carbon atoms and from 1 to 3 oxygen or sulphur atoms, such as methoxymethyl ether, methoxyethoxymethyl ether or methylthiomethyl ether radicals.

The term "halogen atom" preferably means a fluorine, bromine or chlorine atom.

Among the compounds of formula (I) above which fall within the context of the present invention, mention may be made in particular of the following:

Ethyl 3-methyl-5-(5,5,8,8-tetramethyl-5,6,7,8-tetrahydronaphthalen-2-ylselenyl)pent-2-en-4-ynoate 3-Methyl-5-(5,5,8,8-tetramethyl-5,6,7,8-tetrahydronaphthalen-2-ylselenyl)pent-2-en-4-ynoic acid Ethyl 3-methyl-5-(3,5,5,8,8-pentamethyl-5,6,7,8-tetrahydronaphthalen-2-ylselenyl)pent-2-en-4-ynoate 3-Methyl-5-(3,5,5,8,8-pentamethyl-5,6,7,8-tetrahydronaphthalen-2-ylselenyl)pent-2-en-4-ynoic acid Ethyl 3-methyl-5-(5,5,8,8-tetramethyl-5,6,7,8-tetrahydronaphthalen-2-ylsulphonyl)pent-2-en-4-ynoate 3-Methyl-5-(5,5,8,8-tetramethyl-5,6,7,8-tetrahydronaphthalen-2-ylsulphonyl)pent-2-en-4-ynoic acid Ethyl 3-methyl-5-(3,5,5,8,8-pentamethyl-5,6,7,8-tetrahydronaphthalen-2-ylsulphonyl)pent-2-en-4-ynoate 3-Methyl-5-(3,5,5,8,8-pentamethyl-5,6,7,8-tetrahydronaphthalen-2-ylsulphonyl)pent-2-en-4-ynoic acid Ethyl 3-methyl-5-(5,5,8,8-tetramethyl-3-propoxy-5,6,7,8-tetrahydronaphthalen-2-ylselenyl)pent-2-en-4-ynoate 3-Methyl-5-(5,5,8,8-tetramethyl-3-propoxy-5,6,7,8-tetrahydronaphthalen-2-ylselenyl)pent-2-en-4-ynoic acid Ethyl 3-methyl-5-(5,5,8,8-tetramethyl-4-propoxy-5,6,7,8-tetrahydronaphthalen-2-ylselenyl)pent-2-en-4-ynoate 3-Methyl-5-(5,5,8,8-tetramethyl-4-propoxy-5,6,7,8-tetrahydronaphthalen-2-ylselenyl)pent-2-en-4-ynoic acid Ethyl 5-(4-methoxymethoxy-5,5,8,8-tetramethyl-5,6,7,8-tetrahydronaphthalen-2-ylselenyl)-3-methylpent-2-en-4-ynoate 5-(4-Methoxymethoxy-5,5,8,8-tetramethyl-5,6,7,8-tetrahydronaphthalen-2-ylselenyl)-3-methylpent-2-en-4-ynoic acid Ethyl 5-(3-hydroxy-5,5,8,8-tetramethyl-5,6,7,8-tetrahydronaphthalen-2-ylselenyl)-3-methylpent-2-en-4-ynoate 5-(3,5,5,8,8-Pentamethyl-5,6,7,8-tetrahydro-naphthalen-2-ylselenyl)-3-phenylpent-2-en-4-ynoic acid 5-(4-Methoxymethoxy-5,5,8,8-tetramethyl-5,6,7,8-tetrahydronaphthalen-2-ylselenyl)-3-phenylpent-2-en-4-ynoic acid Methyl 5-(4-hydroxy-5,5,8,8-tetramethyl-5,6,7,8-tetrahydronaphthalen-2-ylselenyl)-3-phenylpent-2-en-4-ynoate 3-Propyl-5-(5,5,8,8-tetramethyl-5,6,7,8-tetrahydronaphthalen-2-ylselenyl)pent-2-en-4-ynoic acid 5-(4-Benzyloxy-3-bromo-5,5,8,8-tetramethyl-5,6,7,8-tetrahydronaphthalen-2-ylselenyl)-3-methylpent-2-en-4-ynoic acid 5-(4-Benzyloxy-5,5,8,8-tetramethyl-5,6,7,8-tetrahydronaphthalen-2-ylselenyl)-3-phenylpent-2-en-4-ynoic acid Ethyl 5-[5-adamantan-1-yl-4-(2-methoxyethoxymethoxy)-2-methylphenylselenyl]-3-methylpent-2-en-4-ynoate 5-[5-Adamantan-1-yl-4-(2-methoxyethoxymethoxy)-2-methylphenylselenyl]-3-methylpent-2-en-4-ynoic acid 5-[5-Adamantan-1-yl-4-(2-methoxyethoxymethoxy)-2-methylphenylselenyl]-3-propylpent-2-en-4-ynoic acid 5-[5-Adamantan-1-yl-4-(2-methoxyethoxymethoxy)-2-methylphenylselenyl]-3-phenylpent-2-en-4-ynoic acid Ethyl 5-(3,5-di-tert-butyl-2-methoxymethoxyphenylselenyl)-3-methylpent-2-en-4-ynoate 5-(3,5-Di-tert-butyl-2-methoxymethoxyphenyl-selenyl)-3-methylpent-2-en-4-ynoic acid Ethyl 3-methyl-5-(5,5,8,8-tetramethyl-3-hexyloxy-5,6,7,8-tetrahydronaphthalen-2-ylselenyl)pent-2-en-4-ynoate 3-Methyl-5-(5,5,8,8-tetramethyl-3-hexyloxy-5,6,7,8-tetrahydronaphthalen-2-ylselenyl)pent-2-en-4-ynoic acid 5-[4-Adamantan-1-yl-3-(2-methoxyethoxymethoxy)-phenylselenyl]-3-propylpent-2-en-4-ynoic acid Ethyl 5-[2-(adamantan-1-yl)-1-methoxyethoxymethoxyphen-5-ylselenyl)-3-methylpent-2-en-4-ynoate Ethyl 5-[4-(2-methoxyethoxymethoxy)-5,5,8,8-tetramethyl-5,6,7,8-tetrahydronaphthalen-2-ylsulphonyl]-3-methylpent-2-en-4-ynoate (Z)-5-[4-(2-Methoxyethoxymethoxy)-5,5,8,8-tetramethyl-5,6,7,8-tetrahydronaphthalen-2-ylsulphonyl]-3-methylpent-2-en-4-ynoic acid (E)-5-[4-(2-Methoxyethoxymethoxy)-5,5,8,8-tetramethyl-5,6,7,8-tetrahydronaphthalen-2-ylsulphonyl]-3-methylpent-2-en-4-ynoic acid Methyl 5-(3,5,5,8,8-pentamethyl-5,6,7,8-tetrahydronaphthalen-2-ylsulphonyl)penta-2,4-diynoate Ethyl 5-(3-benzyloxy-5,5,8,8-tetramethyl-5,6,7,8-tetrahydronaphthalen-2-ylselenyl)-3-methylpent-2-en-4-ynoate 5-(3-Benzyloxy-5,5,8,8-tetramethyl-5,6,7,8-tetrahydronaphthalen-2-ylselenyl)-3-methylpent-2-en-4-ynoic acid Ethyl 5-[3-(2-methoxyethoxymethoxy)-5,5,8,8-tetramethyl-5,6,7,8-tetrahydronaphthalen-2-ylselenyl]-3-methylpent-2-en-4-ynoate 5-[3-(2-Methoxyethoxymethoxy)-5,5,8,8-tetramethyl-5,6,7,8-tetrahydronaphthalen-2-ylselenyl]-3-methylpent-2-en-4-ynoic acid Methyl 5-(3,5,5,8,8-pentamethyl-5,6,7,8-tetrahydronaphthalen-2-ylselenyl)penta-2,4-diynoate Ethyl 5-(4-benzyloxy-5,5,8,8-tetramethyl-5,6,7,8-tetrahydronaphthalen-2-ylselenyl)-3-methylpent-2-en-4-ynoate Ethyl 5-[3-[5-(tert-butyldimethylsilanyloxy)-pentyloxymethyl]-5,5,8,8-tetramethyl-5,6,7,8-tetrahydronaphthalen-2-ylselenyl]-3-methylpent-2-en-4-ynoate 5-[3-[5-(tert-Butyldimethylsilanyloxy)pentyl-oxymethyl]-5,5,8,8-tetramethyl-5,6,7,8-tetrahydronaphthalen-2-ylselenyl]-3-methylpent-2-en-4-ynoic acid Ethyl 5-[3-(5-hydroxypentyloxy)-5,5,8,8-tetramethyl-5,6,7,8-tetrahydronaphthalen-2-ylselenyl]-3-methylpent-2-en-4-ynoate 5-(4-Fluoro-3-methylphenylselenyl)-3-methlpent-2-en-4-ynoic acid 3-Methyl-5-p-tolylselenylpent-2-en-4-ynoic acid 5-(6-Bromo-4,4-dimethylthiochroman-8-ylselenyl)-3-methylpent-2-en-4-ynoic acid.

According to the present invention, the compounds of formula (I) which are more particularly preferred are those for which at least one, and preferably all, of the following conditions is (are) satisfied:

$R_1$ represents a radical —$COR_6$;

X represents an Se or S radical;

the group —X—Y—$R_1$ is in the para position relative to the substituent $R_3$ on the aromatic ring;

$R_2$ and $R_3$, taken together, form, with the adjacent aromatic ring, a 5- or 6-membered ring optionally substituted with methyl groups and/or optionally interrupted by an oxygen or sulphur atom, or $R_2$ or $R_3$ is a 1-adamantyl radical.

A subject of the present invention is also processes for preparing the compounds of formula (I), in particular according to the reaction schemes given in FIGS. 1 and 2.

With reference to FIG. 1, the derivatives of formula (Ia) can be prepared by a sequence of reactions comprising the action of a base such as potassium hydride or sodium hydride on the product (1), followed by coupling with trichloroethylene. The product (2) obtained is subjected to the action of a lithiated base such as BuLi in a solvent such as THF. The acetylene derivative (3) obtained can be coupled with a disubstituted alkyne in the presence of a palladium catalyst.

With reference to FIG. 2, the derivatives of formula (Ib) can be prepared by a sequence of reactions comprising the action of a lithiated base such as tBuLi on the product (4) in a solvent such as THF, followed by the addition of selenium and the formation of the dimer by oxidation in basic medium (EtOH, NAOH). The product (5) obtained is subjected to the action of bromine in a solvent such as THF and is then coupled with a true acetylene derivative in the presence of a copper catalyst.

The product (Ia) with Y other than an oxygen atom can be oxidized to sulphone or sulphoxide by the action of an oxidizing agent such as meta-perbenzoic acid or sodium periodate.

When $R_1$ represents a COOH radical, the compounds are prepared by protecting $R_1$ with a protecting group of alkyl type. Saponification of the ester function in the presence of a base such as sodium hydroxide or lithium hydroxide in an alcoholic solvent or in THF gives the corresponding acids.

When $R_1$ represents an alcohol radical, the compounds can be obtained from the acid by reduction in the presence of hydride such as boron hydride. The alcohol can be etherified according to the standard methods.

When $R_1$ represents an aldehyde radical, the compounds can be obtained by oxidation of the corresponding alcohols by the action of manganese oxide or pyridinium dichromate.

When $R_1$ represents an amide radical, the compounds can be obtained by conversion of the acid to the acid chloride, followed by reaction with a suitable amine.

These compounds bind to the RXR receptors, some having agonist activity, others having antagonist activity. Some of these compounds can also bind to the RAR receptors.

The binding and transactivation properties as RXR-receptor agonists can be determined by methods known in the art, such as, for example: Levin et al., Nature 1992, 355, 359–61; Allenby et al., Proc. Natl. Acad. Sci., 1993, 90, 30–4.

The RXR-agonist activity can also be determined by the test described in French patent application No. 95/07301 filed on Jun. 19, 1995 by the Applicant. This test comprises the following steps: (i) a sufficient amount of a compound which is an active ligand for at least one receptor of the superfamily of steroidal/thyroid nuclear receptors other than a ligand specific for the RXR receptors and which can heterodimerize with the RXRs, such as an RAR-agonist molecule, is applied topically to a part of the skin of a mammal, (ii) a molecule capable of having RXR-agonist activity is administered systemically or topically to this same part of the skin of the mammal before, during or after step (i), and (iii) the response on the part of the mammal's skin thus treated is evaluated. Thus, the response to a topical application to a mammal's ear of an RAR-agonist molecule which corresponds to an increase in the thickness of this ear can be increased by the systemic or topical administration of an RXR-receptor agonist molecule.

The RXRa-antagonist activity can be evaluated in the transactivation test by determination of the dose ($IC_{50}$) which gives 50% inhibition of the transactivating activity of an RXRa-selective agonist: 6-[1-(3,5,5,8,8-pentamethyl-5,6,7,8-tetrahydro-2-naphthyl)cyclopropyl]nicotinic acid (CD 3127) according to the following procedure:

HeLa cells are co-transfected with an expression vector coding for RXRa (p565-RXRa) and a reporter plasmid containing the response element 1/2 CRBP II cloned upstream of the thymidine kinase heterologous promoter and of the chloramphenicolmacetyl-transferase (CAT) reporter gene. Eighteen hours after co-transfection, the cells are treated with a fixed concentration of CD 3127 and increasing concentrations of the molecule to be evaluated. After treatment for twenty-four hours, the CAT activity is assayed by ELISA. The fixed concentration of CD3127 used is $10^{-8}M$ and corresponds to its $EC_{50}$.

A subject of the present invention is thus, as a medicinal product, the compounds of formula (I) as defined above.

The compounds according to the invention are particularly suitable in the following fields of treatment:
1) for treating dermatological complaints associated with a keratinization disorder which has a bearing on differentiation and on proliferation, in particular for treating common acne, comedones, polymorphonuclear leukocytes, rosacea, nodulocystic acne, acne conglobata, senile acne and secondary acnes such as solar, medication-related or occupational acne,
2) for treating other types of keratinization disorder, in particular ichthyosis, ichthyosiform states, Darier's disease, palmoplantar keratoderma, leucoplasias and leucoplasiform states, and cutaneous or mucous (buccal) lichen,
3) for treating other dermatological complaints associated with a keratinization disorder with an inflammatory and/or immunoallergic component and, in particular, all forms of psoriasis, whether it is cutaneous, mucous or ungual psoriasis, and even psoriatic rheumatism, or alternatively cutaneous atopy, such as eczema or respiratory atopy or alternatively gingival hypertrophy; the compounds can also be used in certain inflammatory complaints which have no keratinization disorder,
4) for treating all dermal or epidermal proliferations, whether benign or malignant and whether they are of viral origin or otherwise, such as common warts, flat warts and verruciform epidermodysplasia, it being also possible for the oral or florid papillomatoses and the proliferations to be induced by ultraviolet radiation, in particular in the case of basocellular and spinocellular epithelioma,
5) for treating other dermatological disorders such as bullosis and collagen diseases,
6) for treating certain ophthalmological disorders, in particular corneopathies,
7) for repairing or combating ageing of the skin, whether this is light-induced or chronological ageing, or for reducing actinic keratoses and pigmentations, or any pathologies associated with chronological or actinic ageing,
8) for preventing or curing the stigmata of epidermal and/or dermal atrophy induced by local or systemic corticosteroids, or any other form of cutaneous atrophy,
9) for preventing or treating cicatrization disorders or for preventing or repairing stretch marks, or alternatively for promoting cicatrization,
10) for combating disorders of sebaceous functioning such as the hyperseborrhoea of acne or simple seborrhoea,
11) in the treatment or prevention of cancerous or precancerous states,
12) in the treatment of inflammatory complaints such as arthritis,
13) in the treatment of any general or skin complaint of viral origin,
14) in the prevention or treatment of alopecia,
15) in the treatment of dermatological or general complaints having an immunological component,
16) in the treatment of complaints of the cardiovascular system such as arteriosclerosis, hypertension, non-insulin-dependent diabetes and obesity,
17) in the treatment of skin disorders due to an exposure to UV radiation.

In the therapeutic fields mentioned above, the compounds according to the invention may be employed advantageously in combination with other compounds of retinoid-type activity, with D vitamins or derivatives thereof, with corticosteroids, with anti-free-radical agents, a-hydroxy or a-keto acids or derivatives thereof, or alternatively ion-channel blockers. The expression "D vitamins or derivatives thereof" means, for example, vitamin $D_2$ or $D_3$ derivatives and in particular 1,25-dihydroxyvitamin $D_3$. The expression "anti-free-radical agents" means, for example, a-tocopherol, superoxide dismutase, ubiquinol or certain metal-chelating agents. The expression "a-hydroxy or a-keto acids or derivatives thereof" means, for example, lactic, malic, citric, glycolic, mandelic, tartaric, glyceric or ascorbic acid or the salts, amides or esters thereof. Lastly, the term "ion-channel blockers" means, for example, Minoxidil (2,4-diamino-6-piperidinopyrimidine 3-oxide) and derivatives thereof.

A subject of the present invention is also medicinal compositions containing at least one compound of formula (I) as defined above, one of the optical or geometrical isomers thereof or one of the salts thereof.

A subject of the present invention is thus a novel medicinal composition intended in particular for treating the above-mentioned complaints, and which is characterized in that it comprises, in a pharmaceutically acceptable support which is compatible with the mode of administration selected for this composition, at least one compound of formula (I), one of the optical or geometrical isomers thereof or one of the salts thereof.

The compounds according to the invention may be administered enterally, parenterally, topically or ocularly.

Via the enteral route, the medicinal products may be in the form of tablets, gelatin capsules, sugar-coated tablets, syrups, suspensions, solutions, powders, granules, emulsions, microspheres or nanospheres or polymeric or lipid vesicles which enable controlled release. Via the parenteral route, the compositions may be in the form of solutions or suspensions for infusion or for injection.

The compounds according to the invention are generally administered at a daily dose of about 0.01 mg/kg to 100 mg/kg of body weight taken in 1 to 3 doses.

Via the topical route, the pharmaceutical compositions based on compounds according to the invention are more particularly intended for the treatment of the skin and the mucosae and may be in the form of ointments, creams, milks, salves, powders, impregnated pads, solutions, gels, sprays, lotions or suspensions. They may also be in the form of microspheres or nanospheres or polymeric or lipid vesicles or polymeric patches and hydrogels which enable controlled release. These topical-route compositions may either be in anhydrous form or in aqueous form, depending on the clinical indication.

Via the ocular route, they are mainly eyedrops.

These compositions for topical or ocular use contain at least one compound of formula (I) as defined above, or one of the optical or geometrical isomers thereof or alternatively one of the salts thereof, at a concentration preferably of between 0.001% and 5% by weight relative to the total weight of the composition.

The compounds of formula (I) according to the invention also find an application in the cosmetic field, in particular in body and hair hygiene and especially for treating skin types with a tendency towards acne, for promoting the regrowth of the hair, for combating hair loss, for combating the greasy appearance of the skin or the hair, in protection against the harmful effects of the sun or in the treatment of physiologically dry skin types, and for preventing and/or combating light-induced or chronological ageing.

In the cosmetic field, the compounds according to the invention can moreover be employed advantageously in combination with other compounds of retinoid-type activity, with D vitamins or derivatives thereof, with corticosteroids, with anti-free-radical agents, a-hydroxy or a-keto acids or derivatives thereof, or alternatively with ion-channel blockers, all of these various products being as defined above.

The present invention is thus also directed towards a cosmetic composition which is characterized in that it comprises, in a cosmetically acceptable support which is suitable for topical application, at least one compound of formula (I) as defined above or one of the optical or geometrical isomers thereof or one of the salts thereof, it being possible for this cosmetic composition to be, in particular, in the form of a cream, a milk, a lotion, a gel, microspheres or nanospheres or polymeric or lipid vesicles, a soap or a shampoo.

The concentration of compound of formula (I) in the cosmetic compositions according to the invention is advantageously between 0.001% and 3% by weight relative to the entire composition.

The medicinal and cosmetic compositions according to the invention can also contain inert additives or even pharmacodynamically or cosmetically active additives or combinations of these additives and, in particular: wetting agents; depigmenting agents such as hydroquinone, azelaic acid, caffeic acid or kojic acid; emollients; moisturizing agents such as glycerol, PEG 400, thiamorpholinone and derivatives thereof, or urea; anti-seborrhoea or anti-acne agents such as S-carboxymethylcysteine, S-benzylcysteamine, the salts and the derivatives thereof, or benzoyl peroxide; antibiotics such as erythromycin and esters thereof, neomycin, clindamycin and esters thereof, and tetracyclines; antifungal agents such as ketoconazole or 4,5-polymethylene-3-isothiazolidones; agents for promoting the regrowth of the hair, such as Minoxidil (2,4-diamino-6-piperidinopyrimidine 3-oxide) and derivatives thereof, Diazoxide (7-chloro-3-methyl-1,2,4-benzothiadiazine 1,1-dioxide) and Phenytoin (5,5-diphenylimidazolidine-2,4-dione); non-steroidal anti-inflammatory agents; carotenoids and, in particular, b-carotene; anti-psoriatic agents such as anthraline and derivatives thereof, and, lastly, eicosa-5,8,11,14-tetraynoic acid and eicosa-5,8,11-triynoic acid, the esters and the amides thereof.

The compositions according to the invention may also contain flavour-enhancing agents, preserving agents such as para-hydroxybenzoic acid esters, stabilizing agents, moisture regulators, pH regulators, osmotic pressure modifiers, emulsifying agents, UV-A and UV-B screening agents, and antioxidants such as a-tocopherol, butylhydroxyanisole or butylhydroxytoluene.

Several examples for obtaining active compounds of formula (I) according to the invention, as well as various concrete formulations based on such compounds, will now be given for illustrative purposes and with no limiting nature. In the text hereinbelow and hereinabove, the percentages are given on a weight basis except where otherwise mentioned.

EXAMPLE 1

Ethyl 3-Methyl-5-(5,5,8,8-tetramethyl-5,6,7,8-tetrahydronaphthalen- 2-ylselenyl)pent-2-en-4-ynoate (a) 5,6,7,8-Tetrahydro-5,5,8,8-tetramethylnaphthalene 2-Diselenide A 1.7 M solution of tert-butyllithium in pentane (37.4 mmol, 22 ml) is added to a solution of 2-bromo-5,6,7,8-tetrahydro-5,5,8,8-tetramethylnaphthalene (4.22 g, 15.8 mmol) in THF (100 ml) at −78° C. over. 10 min. The mixture is stirred at 0° C. for 30 min. Selenium (1.33 g, 16.8 mmol) is added in 2 portions. The mixture is stirred at 0° C. for 15 min and then at room temperature for 30 min. 1N HCl solution (40 ml) is added and the reaction mixture is then treated with ethyl ether. The organic phase is washed twice with water, dried over anhydrous magnesium sulphate and concentrated on a rotary evaporator under vacuum at 40° C. 10 ml of ethanol and 50 mg of sodium hydroxide are added to the oil obtained. The mixture is stirred vigorously for a few minutes in air (qs quantitative precipitation) and is then concentrated on a rotary evaporator under vacuum at 40° C. The solid obtained is filtered through silica (eluted with heptane) and then crystallized from an ethanol/ether mixture.

Orange solid. Mass: 2.9 g. Yield: 69%. $^1$H NMR (CDCl$_3$): 1.21 (6H, s), 1.25 (6H, s), 1.65 (4H, s), 7.20 (1H Ar, d, J=8.25 Hz), 7.38 (1H Ar, dd, J=1.9 Hz, J=8.25 Hz), 7.51 (1H Ar, d, J=1.9 Hz).

(b) Ethyl 3-Methylpent-2-en-4-ynoate

KF (58 mg, 1 mmol) is added to a solution of ethyl 3-methyl-5-trimethylsilanylpent-2-en-4-ynoate (J. Am. Chem. Soc. 1997, 119, 698–708), (210 mg, 1 mmol) in 10 ml of methanol, 10 ml of THF and 1 ml of water. The mixture is stirred for 8 h at room temperature. It is then treated with ethyl ether. The organic phase is washed several times with water, dried over anhydrous magnesium sulphate and concentrated.

SiO$_2$ column (30 dichloromethane/70 heptane). Oil. Mass: 100 mg. Yield: 72%. $^1$H NMR (CDCl$_3$): 0.00 (9H, s), 1.05–1.08 (3H, t), 2.06 (3H, s), 3.91–4.00 (2H, q), 5.88–5.89 (1H, m).

(c) Ethyl 3-Methyl-5-(5,5,8,8-tetramethyl-5,6,7,8-tetrahydronaphthalen-2-ylselenyl)pent-2-en-4-ynoate Bromine (0.048 ml, 0.93 mmol) is added to a solution of 5,6,7,8-tetrahydro-5,5,8,8-tetramethyl-naphthalene 2-diselenide (500 mg, 0.94 mmol) in THF (1 ml). The mixture is stirred at room temperature for 2 h and the solvent is then removed with a strong stream of nitrogen. Copper iodide (CuI) (715 mg, 3.75 mmol), ethyl 3-methylpent-2-en-4-ynoate (232 mg, 1.67 mmol) and DMF (5 ml) are added. The reaction mixture is stirred at room temperature for 3 h and is then treated with ethyl ether and aqueous ammonia solution. The organic phase is washed twice with water, dried over anhydrous magnesium sulphate and concentrated on a rotary evaporator under vacuum at 40° C.

SiO$_2$ column (70 heptane/30 dichloromethane) Colourless oil. Mass: 500 mg. Yield: 74%. $^1$H NMR (CDCl$_3$): 1.27 (6H, s), 1.28 (6H, s), 1.25–1.31 (3H, t), 1.68 (4H, s), 2.34 (3H, d), 4.12–4.21 (2H, q), 6.01–6.02 (1H, d), 7.27–7.28 (2H Atr d), 7.45 (1H Ar, s).

EXAMPLE 2

3-Methyl-5-(5,5,8,8-tetramethyl-5,6,7,8-tetrahydro-naphthalen-2-ylselenyl)pent-2-en-4-ynoic acid Lithium hydroxide (500 mg) is added to a solution of ethyl 3-methyl-5-(5,5,8,8-tetramethyl-5,6,7,8-tetrahydronaphthalen-2-ylselenyl)pent-2-en-4-ynoate (500 mg, 1.24 mmol) in 10 ml of THF. 2 ml of a water/methanol mixture (1/1) are added. The reaction medium is refluxed for 8 h. It is then poured into an ethyl ether/water mixture, acidified to pH 1 with concentrated hydrochloric acid solution and extracted with ethyl ether. After separation of the phases by settling, the organic phase is washed twice with water, dried over anhydrous magnesium sulphate and concentrated on a rotary evaporator under vacuum at 40° C.

Yellowish powder. Mass: 270 mg. Yield: 58%. m.p.: 130° C. $^1$H NMR (CDCl$_3$): 1.27 (6H, s), 1.28 (6H, s), 1.68 (4H, s), 2.35 (3H, d), 6.03 (1H, d), 7.28 (2H Ar, s), 7.45 (1H Ar, s).

EXAMPLE 3

Ethyl 3-Methyl-5-(3,5,5,8,8-pentamethyl-5,6,7,8-tetrahydronaphthalen-2-ylselenyl)pent-2-en-4-ynoate (a) 5,6,7,8-Tetrahydro-3,5,5,8,8-pentamethylnaphthalene 2-Diselenide In a manner similar to that of Example 1(a), by reaction of 4.4 g (15.8 mmol) of 2-bromo-5,6,7,8-tetrahydro-3,5,5,8,8-pentamethylnaphthalene with 22 ml of tert-butyllithium and selenium (1.33 g, 16.8 mmol) in 100 ml of THF, 3.26 g (74%) of the expected selenium derivative are obtained in the form of a yellow solid.

(m.p.: 126° C.). $^1$H NMR (CDCl$_3$): 1.14 (6H, s), 1.23 (6H, s), 1.61 (4H, s), 2.35 (3H, s), 7.05 (1H Ar, s), 7.55 (1H Ar, s).

(b) Ethyl 3-Methyl-5-(3,5,5,8,8-pentamethyl-5,6,7,8-tetrahydronaphthalen-2-ylselenyl)pent-2-en-4-ynoate In a manner similar to that of Example 1(c), by reaction of 530 mg (0.94 mmol) of 5,6,7,8-tetrahydro-3,5,5,8,8-pentamethylnaphthalene 2-diselenide in 1 ml of THF, with bromine (0.048 ml, 0.93 mnmol), copper iodide (715 mg, 3.75 mnmol), ethyl 3-methylpent-2-en-4-ynoate (232 mg, 1.68 mmol) in 5 ml of DMF, 690 mg (88%) of the expected ester derivative are obtained in the form of an oil.

$^1$H NMR (CDCl$_3$): 1.26 (6H, s), 1.29 (6H, s), 1.25–1.31 (3H, t), 1.67 (4H, s), 2.31 (3H, s), 2.35–2.36 (3H, d), 4.12–4.21 (2H, q), 6.02–6.03 (1H, d), 7.10 (1H Ar, s), 7.62 (1H Ar, s).

EXAMPLE 4

3-Methyl-5-(3,5,5,8,8-pentamethyl-5,6,7,8-tetrahydronaphthalen-2-ylselenyl)pent-2-en-4-ynoic Acid In a manner similar to that of Example 2, by reaction of 600 mg of ethyl 3-methyl-5-(3,5,5,8,8-pentamethyl-5,6,7,8-tetrahydronaphthalen-2-ylselenyl)-pent-2-en-4-ynoate with 600 mg of LiOH in 15 ml of THF, 410 mg (73%) of a yellow powder are obtained. m.p.: 175° C.

$^1$H NMR (CDCl$_3$): 1.26 (6H, s), 1.29 (6H, s), 1.67 (4H, s), 2.32 (3H, s), 2.36–2.37 (3H, d), 6.04 (1H, d), 7.10 (1H Ar, s), 7.62 (1H Ar, s).

EXAMPLE 5

Ethyl 3-Methyl-5-(5,5,8,8-tetramethyl-5,6,7,8-tetrahydronaphthalen-2-ylsulphonyl)pent-2-en-4-ynoate (a) 6-(2,2-Dichlorovinylsulphonyl)-1,1,4,4-tetramethyl-1,2,3,4-tetrahydronaphthalene 5,6,7,8-Tetrahydro-5,5,8,8-tetramethylnaphthalene 2-disulphide (J. Med. Chem. 1995, 38, 3171) (17.5 g, 79.5 mol) in 100 ml of THF is added to a suspension of 35% potassium hydride (19.77 g) in 300 ml of THF. The mixture is stirred for 1 h at room temperature and then cooled to −50° C. A solution of trichloroethylene (7.9 ml) in 100 ml of THF is then added dropwise thereto. The mixture is allowed to warm to room temperature and is stirred for 1 h. The mixture is then concentrated, after which it is treated with ethyl ether. The organic phase is washed several times with water, dried over anhydrous magnesium sulphate and concentrated.

Brown oil. Mass: 25 g. Yield: 100% $^1$H NMR (CDCl$_3$): 1.17 (6H, s), 1.18 (6H, s), 1.58 (4H, s), 6.41 (1H, s), 7.06–7.10 (1H Ar, dd, J=2.04 Hz, J'=6.2 Hz), 7.17–7.20 (1H Ar, d, J=8.25 Hz), 7.26–7.27 (1H Ar, d, J=2 Hz).

(b) 6-Ethynylsulphonyl-1,1,4,4-tetramethyl-1,2,3,4-tetrahydronaphthalene

A solution of 6-(2,2-dichlorovinylsulphonyl)-1,1,4,4-tetramethyl-1,2,3,4-tetrahydronaphthalene (7 g; 22.2 mmol) in 70 ml of THF is cooled to −70° C. and then treated with 2.5 M n-butyllithium/hexane (19.5 ml; 48.8 mmol). The mixture is allowed to warm to room temperature and is stirred for 3 h. The mixture is concentrated and then treated with ethyl ether. The organic phase is washed several times with water, dried over anhydrous magnesium sulphate and concentrated on a rotary evaporator under vacuum at 40° C.

SiO$_2$ column (heptane) Yellow oil. Mass: 3.4 g. Yield: 63%. $^1$H NMR (CDCl$_3$): 1.26 (6H, s), 1.27 (6H, s), 1.67 (4H, s), 3.19 (1H, s), 7.20–7.24 (1H Ar, dd, J=2.02 Hz, J'=6.33 Hz), 7.27–7.31 (1H-Ar, d, J=8.32 Hz), 7.35–7.36 (1H Ar, d, J=2 Hz).

(c) Ethyl 3-Methyl-5-(5,5,8,8-tetramethyl-5,6,7,8-tetrahydronaphthalen-2-ylsulphonyl)pent-2-en-4-ynoate In a manner similar to that of J. Am. Chem. Soc. 1997, 119, 698–708, by reaction of Pd(OAc)$_2$ (22 mg, 0.098 mmol), tris(2,6-dimethoxyphenyl)phosphine [TDMPP] (44 mg), ethyl 2-butynoate (650 mg, 5.8 mmol) and 6-ethynylsulphonyl,1,4,4-tetramethyl-1,2,3,4-tetrahydronaphthalene (800 mg, 3.27 mmol) in 18 ml of toluene, 603 mg (52%) of the expected product are obtained in the form of a yellow oil.

$^1$H NMR (CDCl$_3$): 1.26 (6H, s), 1.28 (6H, s), 1.25–1.31 (3H, t), 1.67 (4H, s), 2.36 (3H, d), 4.13–4.21 (2H, q), 6.00–6.02 (1H, d), 7.16–7.20 (1H Ar, dd, J=2.12 Hz, J'=6.27 Hz), 7.29–7.32 (1H Ar, d, J=8.35 Hz), 7.34–7.35 (1H Ar, d, J=2.1 Hz).

EXAMPLE 6

3-Methyl-5-(5,5,8,8-tetramuet-5,6,7,8-tetrahydro-naphthalen-2-ylsulphonyl)pent-2-en-4-ynoic Acid NaOH (100 mg, 2.5 mmol) in water is added to a solution of ethyl 3-methyl-5-(5,5,8,8-tetramethyl-5,6,7,8-tetrahydronaphthalen-2-ylsulphonyl)pent-2-en-4-ynoate (605 mg, 1.7 mmol) in 15 ml of THF. The medium is then refluxed for 6 h. Next, it is poured into an ethyl ether/water mixture, acidified to pH 1 with concentrated hydrochloric acid solution and extracted with ethyl ether. After separation of the phases by settling, the organic phase is washed twice with water, dried over anhydrous magnesium sulphate and concentrated on a rotary evaporator under vacuum at 40° C. The residue is then crystallized from methanol.

Yellowish powder. Mass: 323 mg. Yield: 58%. m.p.: 134° C. $^1$H NMR (CDCl$_3$): 1.27 (6H, s), 1.28 (6H, s), 1.68 (4H, s), 2.37–2.38 (3H, d), 6.02–6.03 (1H, d), 7.17–7.21 (1H Ar, dd, J=2.08 Hz, J'=6.3 Hz), 7.30–7.33 (1H Ar, d, J=8.38 Hz), 7.35–7.36 (1H Ar, d, J=2.04 Hz).

EXAMPLE 7

Ethyl 3-Methyl-5-(3,5,5,8,8-pentamethyl-5,6,7,8-tetrahydronaphthalen-2-ylsulphonyl)pent-2-en-4-ynoate (a) 6-(2,2-Dichlorovinylsulphonyl)-1,1,4,4,7-pentamethyl-1,2,3,4-tetrahydronaphthalene In a manner similar to that of Example 5(a), by reaction of 3,5,5,8,8-pentamethyl-5,6,7,8-tetrahydronaphthalene-2-thiol (15 g, 64.1 mmol) in 500 ml of THF with 35% potassium hydride (11 g, 96.1 mmol) and trichloroethylene (6.91 ml, 76.9 mmol), 16.1 g (87%) of the expected dichloro derivative are obtained in the form of a colourless oil.

$^1$H NMR (CDCl$_3$): 1.27 (12H, s), 1.67 (4H, s), 2.36 (3H, s), 6.46 (1H, s), 7.15 (1H, s), 7.38 (1H, s).

(b) 6-Ethynylsulphonyl-1,1,4,4,7-pentamethyl-1,2,3,4-tetrahydronaphthalene

In a manner similar to that of Example 5(b), by reaction at −78° C. of 6-(2,2-dichlorovinylsulphonyl)-1,1,4,4,7-pentamethyl-1,2,3,4-tetrahydronaphthalene (8 g, 24.3 mmol) in 200 ml of THF with 2.5 M n-butyllithium/hexane (21.4 ml, 53.5 mmol), 2.08 g (33%) of the expected alkyne are obtained in the form of a yellow solid.

$^1$H NMR (CDCl$_3$): 1.27 (12H, s), 1.67 (4H, s), 2.30 (3H, s), 3.15 (1H, s), 7.09 (1H, s), 7.58 (1H, s).

(c) Ethyl 3-Methyl-5-(3,5,5,8,8-pentamethyl-5,6,7,8-tetrahydronaphthalen-2-ylsulphonyl)pent-2-en-4-ynoate In a manner similar to that of Example 5(c), by reaction of 6-ethynylsulphonyl-1,1,4,4,7-pentamethyl-1,2,3,4-tetrahydronaphthalene (2.08 g, 151 mmol) in 60 ml of toluene with Pd(OAc)$_2$ (70 mg, 0.3 mmol), TDMPP (140 mg) and ethyl 2-butynoate (2.05 g, 20.9 mmol), 1 g (27%) of the expected ester is obtained in the form of a brown oil.

$^1$H NMR (CDCl$_3$): 1.29 (12H, m), 1.67 (4H, s), 2.30 (3H, s), 2.37 (3H, s), 4.17 (2H, q), 6.01 (1H, d), 7.10 (1H, s), 7.53 (1H, s).

EXAMPLE 8

3-Methyl-5-(3,5,5,8,8-pentamethyl-5,6,7,8-tetrahydronaphthalen-2-ylsulphonyl)pent-2-en-4-ynoic Acid Sodium hydroxide (400 mg, 10 mmol) is added to a solution of ethyl 3-methyl-5-(3,5,5,8,8-pentamethyl-5,6,7,8-tetrahydronaphthalen-2-ylsulphonyl)pent-2-en-4-ynoate (400 mg, 1.6 mmol) in 15 ml of THF. The medium is refluxed for 4 h. It is then poured into an ethyl ether/water mixture, acidified to pH 1 with concentrated hydrochloric acid solution and extracted with ethyl ether. After separation of the phases by settling, the organic phase is washed twice with water, dried over anhydrous magnesium sulphate and concentrated on a rotary evaporator under vacuum at 40° C. The residue is then triturated from heptane, after which it is filtered.

Brown solid. Mass: 240 mg. Yield: 44%. m.p.: 165° C. $^1$H NMR (CDCl$_3$): 2.31 (3H, s), 2.38 (3H, d), 6.02 (1H, d), 7.10 (1H, s), 7.53 (1H, s).

EXAMPLE 9

Ethyl 3-Methyl-5-(5,5,8,8-tetramethyl-3-propoxy-5,6,7,8-tetrahydronaphthalen-2-ylselenyl)pent-2-en-4-ynoate a) 5,5,8,8-Tetramethyl-3-propoxy-5,6,7,8-tetrahydronaphthalen-2-yl Diselenide In a manner similar to that of Example 1(a), starting with 6 g of 2-bromo-5,5,8,8-tetramethyl-3-propoxy-5,6,7,8-tetrahydronaphthalene, 3.2 g (55%) of the expected compound are obtained in the form of an orange-coloured powder. m.p.=94° C.

b) Ethyl 3-Methyl-5-(5,5,8,8-tetramethyl-3-propoxy-5,6,7,8-tetrahydronaphthalen-2-ylselenyl)pent-2-en-4-ynoate In a manner similar to that of Example 1(c), starting with 380 mg of ethyl 3-methylpent-2-en-4-ynoate and 1 g of the product obtained above, 740 mg (58%) of the expected compound are obtained in the form of a beige powder. m.p.=58° C.

$^1$H NMR (CDCl$_3$): 1.05 (t, 3H); 1.27 to 1.32 (m; 12H); 1.68 (s, 4H); 1.80 (sext, 2H); 2.41 (d, 3H); 3.97 (t, 2H); 6.06 (d, 1H); 6.72 (s, 1H); 7.26 (s, 1H); 7.54 (s, 1H); $^{13}$C NMR (CDCl$_3$): 11.0; CH$_3$/14.6; CH$_3$/20.1; CH$_3$/22.9; CH$_2$/32.3; 4*CH$_3$/34.5; Cq/34.9; Cq/35.4; 2*CH$_2$/60.4; CH$_2$/70.6; CH$_2$/77.6; Cq/107.3; Cq/109.5; CH/115.3; Cq/122.6; CH/126.8; CH/137.7; Cq/139.2; Cq/145.6; Cq/153.6; Cq/166.6; Cq.

EXAMPLE 10

3-Methyl-5-(5,5,8,8-tetramethyl-3-propoxy-5,6,7,8-tetrahydronaphthalen-2-ylselenyl)pent-2-en-4-ynoic Acid In a manner similar to that of Example 2, starting with 570 mg of the product of Example 9, 390 mg (73%) of the expected compound are obtained in the form of a beige powder. m.p.=170° C.

$^1$H NMR/CDCl$_3$: 1.05 (t, 3H); 1.28 (m, 12H); 1.67 (s, 4H); 2.39 (d, 3H); 3.97 (t, 2H); 6.07 (d, 1H); 6.72 (s, 1H); 7.54 (s, 1H): $^{13}$C NMR/CDCl$_3$: 11.0; CH$_3$/20.1; CH$_3$/22.9; CH$_2$/32.2; 2*CH$_3$/32.4; 2*CH$_3$/34.5; Cq/34.9; Cq/35.4; 2*CH$_2$/70.6; CH$_2$/107.4; Cq/109.5; CH/115.3; Cq/123.3; CH/126.8; CH/137.5; Cq/139.3; Cq/145.6; Cq/153.5; Cq/168.5; Cq.

EXAMPLE 11

Ethyl 3-Methyl-5-(5,5,8,8-tetramethyl-4-propoxy-5,6,7,8-tetrahydronaphthalen-2-ylselenyl)pent-2-en-4-ynoate a) 5,5,8,8-Tetramethyl-4-propoxy-5,6,7,8-tetrahydronaphthalen-2-yl Diselenide In a manner similar to that of Example 1(a), starting with 3.8 g of 2-bromo-5,5,8,8-tetramethyl-4-propoxy-5,6,7,8-tetrahydronaphthalene, 1.8 g (47%) of the expected compound are obtained in the form of an orange-coloured powder. m.p.=75° C.

b) Ethyl 3-Methyl-5-(5,5,8,8-tetramethyl-4-propoxy-5,6,7,8-tetrahydronaphthalen-2-ylselenyl)pent-2-en-4-ynoate.

In a manner similar to that of Example 1(c), starting with 380 mg of ethyl 3-methylpent-2-en-4-ynoate and 1.1 g of the product obtained above, 900 mg (70%) of the expected compound are obtained in the form of a yellow oil.

$^1$H NMR/CDCl$_3$: 1.08't, 3H); 1.27 (m, 6H); 1.39 (s, 6H); 1.63 (m, 4H); 1.87 (sext, 2H); 2.35 (d, 3H); 3.90 (t, 2H); 4.16 (q, 2H); 6.01 (d, 1H); 6.85 (d, 1H); 7.07 (d, 1H); $^{13}$C NMR/CDCl$_3$: 10.7; CH$_3$/13.9; CH$_3$/19.2; CH$_3$/22.4; CH$_2$/28.0; 2*CH$_3$/31.6; 2*CH$_3$/34.0; Cq/34.5; CH$_2$/34.7; Cq/37.6; CH$_2$/59.7; CH$_2$/69.5; CH$_2$/77.3; Cq/105.2; Cq/109.6; CH/119.8; CH/122.0; CH/132.3; Cq/136.9; Cq/148.4; Cq/158.5; Cq/165.8; Cq.

EXAMPLE 12

3-Methyl-5-(5,5,8,8-tetramethyl-4-propoxy-5,6,7,8-tetrahydronaphthalen-2-ylselenyl)pent-2-en-4-ynoic Acid In a manner similar to that of Example 2, starting with 750 mg of the product of Example 11, 430 mg (61%) of the expected compound are obtained in the form of a beige powder. m.p.=164° C.

$^1$H NMR/CDCl$_3$: 1.09 (t, 3H); 1.27 (S, 6H); 1.38 (s, 6H); 1.63 (m, 4H); 1.88 (sext, 2H); 2.36 (d, 3H); 3.93 (t, 2H); 6.02 (d, 1H); 6.84 (d, 1H); 7.08 (d, 1H); $^{13}$C NMR/CDCl$_3$: 11.3; CH$_3$/20.2; CH$_3$/22.9; CH$_2$/28.6; 2*CH$_3$/32.1; 2*CH$_3$/34.5; Cq/35.0; Cq/35.3; CH$_2$/38.1; CH$_2$/70.0; CH$_2$/80.4; Cq/105.7; Cq/110.2; CH/120.5; CH/121.4; CH/133.0; Cq/140.4; Cq/149.05; Cq/159.1; Cq/171.3; Cq.

EXAMPLE 13

Ethyl 5-(4-methoxymethoxy-5,5,8,8-tetramethyl-5,6,7,8-tetrahydronaphthalen-2-ylselenyl)-3-methylpent-2-en-4-ynoate a) 4-Methoxymethoxy-5,6,7,8-tetrahydro-5,5,8,8-tetramethylnaphthalene 2-Diselenide In a manner similar to that of Example 1(a), starting with 4 g of 2-bromo-5,5,8,8-tetramethyl-4-methoxymethoxy-5,6,7,8-tetrahydronapthalene, 2.4 g (61%) of the expected compound are obtained inthe form of an orange-coloured powder. m.p.=91° C.

b) Ethyl 5-(4-Methoxymethoxy-5,5,8,8-tetramethyl-5,6,7,8-tetrahydronaphthalen-2-ylselenyl)-3-methylpent-2-en-4-ynoate In a manner similar to that of Example 1(c), starting with 400 mg of ethyl 3-methylpent-2-en-4-ynoate and 800 mg of the product obtained above, 648 mg (96%) of the expected compound are obtained in the form of a brown solid. m.p.=50° C.

$^1$H NMR/CDCl$_3$: 1.25 to 1.28 (m, 9H); 1.39 (s, 6H); 1.63 (m, 4H); 2.35 (d, 3H); 3.50 (3H); 4.16 (q, 2H); 5.21 (s, 2H); 6.06 (d, 1H); 7.12 (d, 1H); 7.17 (d, 1H); $^{13}$C NMR/CDCl$_3$: 14.5; CH$_3$/19.7; CH$_3$/28.7; 2*CH$_3$/32.1; 2*CH$_3$/34.6; Cq/35.0; CH$_2$/35.3; Cq/38.0; CH$_2$/56.3; CH$_3$/60.2; 0H$_2$/77.7; Cq/94.6; CH$_2$/106.1; Cq/112.6; CH/121.2; CH/122.6; CH/125.5; Cq/133.1; Cq/137.5; Cq/149.0; Cq/157.6; Cq/166.4; Cq.

EXAMPLE 14

5-(4-Methoxymethoxy-5,5,8,8-tetramethyl-5,6,7,8-tetrahydronaphthalen-2-ylselenyl)-3-methylpent-2-en-4-ynoic Acid In a manner similar to that of Example 2, starting with 440 mg of the product of Example 13, 330 mg (80%) of the expected compound are obtained in the form of a beige powder. m.p.=130° C.

$^1$H NMR/CDCl$_3$: 1.27 (s, 6H); 1.38 (s, 6H); 1.64 (m, 4H); 2.36 (d, 3H); 3.50 (s, 3H); 5.21 (s, 2H); 6.09 (d, 1H); 7.11 (d, 1H); 7.18 (d, 1H); $^{13}$C NMR/CDCl$_3$: 19.9; CH$_3$/28.6; 2*CH$_3$/32.0; 2*CH$_3$/34.5; CH$_2$/34.8; Cq/35.2; Cq/37.9; CH$_2$/56.2; CH$_3$/79.8; Cq/94.5; CH$_2$/106.2; Cq/112.5; CH/121.2; CH$_2$/121.4; CH$_2$/125.3; Cq/133.2; Cq/140.3; Cq/149.0; Cq/157.6; Cq/171.4; Cq.

EXAMPLE 15

Ethyl 5-(3-Hydroxy-5,5,8,8-tetramethyl-5,6,7,8-tetrahydronaphthalen-2-ylselenyl)-3-methylpent-2-en-4-ynoate a) 3-Methoxymethoxy-5,6,7,8-tetrahydro-5,5,8,8-tetramethylnaphthalene 2-Diselenide In a manner similar to that of Example 1(a), starting with 13.5 g of 2-bromo-5,5,8,8-tetramethyl-3-methoxymethoxy-5,6,7,8-tetrahydronaphthalene, 5.85 g (43%) of the expected compound are obtained in the form of an orange-coloured powder. m.p.=95° C.

b) 3-Hydroxy-5,6,7,8-tetrahydro-5,5,8,8-tetramethylnaphthalene 2-Diselenide

A mixture of the product of Example 15(a) (200 mg), concentrated sulphuric acid (1.4 ml), methanol (20 ml) and THF (20 ml) is stirred for 6 h at room temperature. The reaction mixture is extracted with ethyl acetate. The organic phase is washed twice with water, dried over magnesium sulphate and concentrated on a rotary evaporator under vacuum. The product is purified by flash chromatography (5 CH$_2$Cl$_2$/5 heptane). 120 mg (63%) of the expected compound are obtained in the form of an orange-coloured powder.

$^1$H NMR/CDCl$_3$: 1.17 (s, 6H); 1.25 (s, 6H); 1.63 (s, 4H); 6.93 (s, 1H); 7.34 (s, 1H).

c) Ethyl 5-(3-Hydroxy-5,5,8,8-tetramethyl-5,6,7,8-tetrahydronaphthalen-2-ylselenyl)-3-methylpent-2-en-4-ynoate In a manner similar to that of Example 1(c), starting with 980 mg of ethyl 3-methylpent-2-en-4-ynoate and 2 g of the product obtained above, 1.29 g (87%) of the expected compound are obtained in the form of a yellow solid. m.p.=50° C.

$^1$H NMR/CDCl$_3$: 1.26 to 1.27 (m, 12H); 1.66 (s, 4H); 2.30 (s, 3H); 4.16 (q, 2H); 5.48 (s, 1H); 6.00 (s, 1H); 6.88 (s, 1H); 7.49 (s, 1H); $^{13}$C NMR/CDCl$_3$: 14.2; CH$_3$/19.5; CH$_3$/31.7; 2*CH$_3$/32.0; 2*CH$_3$/34.0; Cq/34.5; Cq/34.8; CH$_2$/35.0; CH$_2$/60.1; CH$_2$/77.2; Cq/103.4; Cq/110.8; Cq/113.4; CH/123.3; CH/131.2; CH/137.0; Cq/139.1; Cq/148.6; Cq/152.2; Cq.

EXAMPLE 16

5-(3,5,5,8,8-Pentamnethyl-5,6,7,8-tetrahydronaphthalen-2-ylselenyl)-3-phenyvlpent-2-en-4-ynoic Acid a) Ethyl 3-Phenyl-5-trimethylsilanylpent-2-en-4-ynoate A solution of TDMPP (1.4 g) and palladium acetate (700 mg) in THF (200 ml) is stirred for 15 min at room temperature and methyl phenylpropiolate (10 g, 62.5 mmol) is then added. The reaction medium is stirred for 5 min at room temperature and trimethylsilylacetylene (87.5 mmol) is then added. Stirring is continued overnight at room temperature. The reaction medium is concentrated and filtered through silica.

$^1$H NMR/CDCl$_3$: 0.28 (s, 9H); 3.67 (s, 3H); 6.45 (s, 1H); 7.39 to 7.41 (m, 3H); 7,48 to 7.51 (m, 2H).

b) Ethyl 3-Phenylpent-2-en-4-ynoate

In a manner similar to that of Example 1(b), the oil obtained above is treated with 10 g of potassium fluoride. 6.8 g (58%) of the expected compound are obtained in the form of a brown oil.

$^1$H NMR/CDCl3: 3.31 (s, 1H): 3.61 (s, 1H): 6.38 (s, 1H); 7.33 to 7.46 (m, 5H); $^{13}$C NMR/CDCl$_3$: 52.0; CH$_3$/83.4; CH/87.1; Cq/126.3; CH/128.4; 2*CH/129.6; 2*CH/131.0; CH/136.1; Cq/137.5; Cq/165.9; Cq.

c) 3-Phenylpent-2-en-4-ynoic Acid

In a manner similar to that of Example 2, starting with 5 g of the above product, 4.8 g (100%) of the expected compound are obtained in the form of an orange-coloured powder. m.p.=130° C.

$^1$H NMR/DMSO: 4.53 (s, 1H); 6.0 (s, 1H); 7.38 (s, 5H) $^{13}$C NMR/DMSO: 84.2; Cq/85.7; Cq/128.2; CH/128.4; CH/128.5; 2*CH/129.2; CH/133.7; Cq/136.1; Cq.

d) 5-(3,5,5,8,8-Pentamethyl-5,6,7,8-tetrahydronaphthalen-2-ylselenyl)-3-phenylpent-2-en-4-ynoic Acid In a manner similar to that of Example 1(c), starting with 1 g of the product obtained above and 1.95 g of 5,6,7,8-tetrahydro-.3,5,5,8,8-pentamethylnaphthalene 2-diselenide, 1.1 g (70%) of the expected compound are obtained in the form of a brown solid.

m.p.=170° C. $^1$H NMR/CDCl$_3$: 1.16 (s, 6H); 1.27 (s, 6H); 1.62 (s, 4H); 2.29 (s, 3H); 6.23 (s, 1H); 7.07 (s, 1H); 7.31 to 7.48 (m, 6H); $^{13}$C NMR/CDCl$_3$: 32.1; 4*CH$_3$/34.4; Cq/34.5; Cq/35.3; 2*CH$_2$/82.1; Cq/104.8; Cq/121.9; CH/125.6; Cq/128.5; CH/129.9; CH/129.0; 3*CH/129.6; 2*CH/134.3; Cq/136.2; Cq/141.3; Cq/144.8; Cq/145.3; Cq/170.7; Cq.

EXAMPLE 17

5-(4-Methoxymethoxy-5,5,8,8-tetramethyl-5,6,7,8-tetrahydronaphthalen-2-ylselenyl)-3-phenylpent-2-en-4-ynoic Acid In a manner similar to that of Example 1(c), starting with 2.12 g of the product obtained in Example 16(c) (3-phenylpent-2-en-4-ynoic acid) and 1.04 g of 4-methoxymethoxy-5,5,8,8-tetramethyl-5,6,7,8-tetrahydro-apthalene 2-diselenide, 700 mg (97%) of the expected compound are obtained in the form of a brown solid.

m.p.=122° C. $^1$H NMR/DMSO: 1.13 (s, 6H); 1.33 (s, 6H); 1.55 to 1.60 (m, 4H); 3.39 (s, 3H); 5.13 (s, 2H); 6.33 (s, 1H); 7.06 (s, 1H); 7.14 (s, 1H); 7.35 to 7.45 (m, 5H); $^{13}$C NMR/DMSO: 28.6; 2*CH3/31.8; 2*CH$_3$/34.3; CH$_2$/34.5 Cq/35.0; Cq/37.6; CH$_{2/56.3}$; CH$_3$/78.3; Cq/94.2, CH$_{2/104.7}$; Cq/112.0; CH/120.6; CH/125.2; Cq/125.3; CH/128.5; 4*CH/129.2; CH/132.3; Cq/135.2; Cq/136.1; Cq/148.8; Cq/157.0; Cq/166.3; Cq.

EXAMPLE 18

Methyl 5-(4-Hydroxy-5,5,8,8-tetramethyl-5,6,7,8-tetrahydronaphthalen-2-ylselenyl)-3-phenylpent-2-en-4-ynoate In a manner similar to that of Example 15(b), starting with 300 mg of the product obtained in Example 17, 60 mg (23%) of the expected compound are obtained in the form of a brown solid. m.p.=93° C.

$^1$H NMR/CDCl$_3$: 1.8 (s, 6H); 1.39 (s, 6H); 1.57 to 1.66 (m, 4H); 3.62 (s, 3H); 4.77 (s, 1H); 6.24 (s, 1H); 6.48 (s, 1H); 6.95 (s, 1H); 7.38 to 7.49 (m, 5H); $^{13}$C NMR/CDCl$_3$: 28.1; 2*CH$_3$/31.9; 2*CH3/34.0; Cq/34.8; CH$_2$/34.9; Cq/37.5; CH$_2$/51.5; CH$_3$/80.2; Cq/104.9; Cq/113.9; CH/121.8; CH/124.8; Cq/128.0; 2*CH/128.7; 2*CH/129.0; CH/130.1; Cq/136.4; Cq/138.6; Cq/149.5; Cq/165.7; Cq.

EXAMPLE 19

3-Propyl-5-(5,5,8,8-tetramethyl-5,6,7,8-tetrahydronaphthalen-2-ylselenyl)pent-2-en-4-ynoic Acid a) Ethyl 5-Trimethylsilyl-3-propylpent-2-en-4-ynoate In a manner similar to that of Example 16(a), starting with 95.2 mmol of trimethylsilylacetylene and 10 g of methyl hexynoate, the expected compound is obtained in the form of a brown oil.

$^1$H NMR/CDCl$_3$: 0.01 (s, 9H); 0.75 (t, 3H); 1.40 (q, 2H); 2.50 (t, 2H); 3.49 (s, 3H); 5.88 (s, 1H); $^{13}$C NMR/CDCl$_3$: 16.0; CH$_3$/17.7; CH$_2$/36.5; CH$_2$/53.6; CH$_3$/68.3; CH/86.6; Cq/127.8; CH/144.4; Cq/168.3; Cq.

b) Ethyl 3-Propylpent-2-en-4-ynoate

In a manner similar to that of Example 16(b), starting with the oil obtained above and 10 g of potassium fluoride, 2.5 g (15%) of the expected compound are obtained in the form of a brown oil.

$^1$H NMR/CDCl$_3$: 0.77 (t, 3H); 1.43 (q, 2H); 2.54 (t, 2H); 3.01 (s, 1H); 3.52 (s, 3H); 5.95 (s, 1H); $^{13}$C NMR/CDCl$_3$: 15.4; CH$_3$/23.4; CH$_2$/35.8; CH$_2$/53.0; CH$_3$/83.8; CH/86.2; Cq/127.1; CH/143.7; Cq/167.7; Cq.

c) 3-Propylpent-2-en-4-ynoic Acid

In a manner similar-to that of Example 16(c), starting with the oil obtained above, 1.86 g (82%) of the expected compound are obtained in the form of a brown solid.

$^1$H NMR/CDCl$_3$: 0.99 (t, 3H); 1.65 (quiint, 2H); 2.74 (t, 2H); 3.275 (s, 1H); 6.16 (s, 1H); $^{13}$C NMR/CDCl$_3$: 15.4; CH$_3$/23.3; CH$_2$/35.8; CH$_2$/84.9; Cq/85.7; CH/126.7; CH/146.3; Cq/172.6; Cq.

d) 3-Propyl-5-(5,5,8,8-tetramethyl-5,6,7,8-tetra-hydronaphthalen-2-ylselenyl)pent-2-en-4-ynoic Acid In a manner similar to that of Example 16(d), starting with 600 mg of the product obtained above and 1.2 g of 5,6,7,8-tetrahydro-3,5,5,8,8-pentamethylnaphthalene 2-diselenide (Example 3a), 800 mg (45%) of the expected compound are obtained in the form of a white solid. m.p.=127° C.

$^1$H NMR/CDCl$_3$: 0.85 (t, 3H); 1.17 (d, 12H); 1.56 (t, 6H); 2.2 (s, 3H); 2.69 (t, 2H); 5.94 (s, 1H); 6.99 (s, 1H); 7.50 ([lacuna], 1H).

EXAMPLE 20

5-(4-Benzyloxy-3-bromo-5,5,8,8-tetramethyl-5,6,7,8-tetrahydronaphthalen-2-ylselenyl)-3-methylpent-2-en-4-ynoic Acid a) 4-Hydroxy-5,6,7,8-tetrahydro-5,5,8,8-tetramethylnaphthalene 2-Diselenide Product 13(a), 4-methoxymethoxy-5,6,7,8-tetrahydro-5,5,8,8-tetramethylnaphthalene 2-diselenide (12.4 g), is treated in a manner similar to that of Example 15(b), and 11 g (100%) of the expected compound are obtained in the form of a white solid. m.p.=200° C.

$^1$H NMR/CDCl$_3$: 1.22 (s, 6H); 1.42 (s. 6H); 1.63 (m, 4H); 5.25 (s, 1H); 6.75 (d, 1H); 7.11 (d, 1H); $^{13}$C NMR/CDCl$_3$: 28.5; 2*CH$_3$/32.2; 2*CH$_3$/34.4; 2*Cq/35.3; CH$_2$/38.0; CH$_2$/116.6; CH/122.6; CH/128.1; Cq/131.5; Cq/149.1; Cq/155.5; Cq.

b) 4-Benzyloxy-5,6,7,8-tetrahydro-5,5,8,8-tetramethylnapthalene 2-Diselenide

A mixture of the product obtained above (2.5 g, 4.4 mmol), caesium carbonate (2.95 g) and benzyl chloride (1.3 ml) in DMF (18 ml) is stirred at room temperature for 24 h. The reaction medium is extracted with ethyl ether. The organic phase is washed with water, dried over magnesium sulphate and concentrated on a rotary evaporator. The product is purified by filtration through silica (heptane and then dichloromethane). 2.1 g (63%) of the expected compound are obtained in the form of a yellow powder.

$^1$H NMR/CDCl$_3$: 1.21 (s, 6H); 1.34 (s, 6H); 1.59 (m, 4H); 4.96 (s, 2H); 7.02 (d, 1H); 7.21 (d, 1H); 7.29 to 7.41 (m, 5H).

c) 3-Methylpent-2-en-4-ynoic Acid

In a manner similar to that of Example 16(c), starting with the product of Example 1(b), the expected compound is obtained in the form of a brown solid.

d) 5-(4-Benzyloxy-3-bromo-5,5,8,8-tetramethyl-5,6,7,8-tetrahydronaphthalen-2-ylselenyl)-3-methylpent-2-en-4-ynoic Acid In a manner similar to that of Example 1(c), starting with 430 mg of the product obtained above and 1 g of 4-benzyloxy-5,6,7,8-tetrahydrb-5,5,8,8-tetramethylnaphthalene 2-diselenide, 100 mg (11%) of the expected compound are obtained in the form of a brown solid.

$^1$H NMR/CDCl$_3$: 1.1 (s, 6H); 1.26 (s, 6H); 1.35 (m, 4H); 2.05 (s, 3H); 4.83 (s, 2H); 5.76 (s, 1H); 6.96 (s, 1H); 7.02 to 7.24 (m, 6H).

EXAMPLE 21

5-(4-Benzyloxy-5,5,8,8-tetramethyl-5,6,7, 8tetrahydronaphthalen-2-ylselenyl)-3-phenylpent-2-en-4-ynoic Acid In a manner similar to that of Example 1(c), starting with 671 mg of 3-phenylpent-2-en-4-ynoic acid (Example 16(c)

and 1 g of 4-benzyloxy-5,6,7,8-tetrahydro-5,5,8,8-tetramethylnaphthalene 2-diselenide, 240 mg (23%) of the expected compound are obtained in the form of a white solid.

$^1$H NMR/THF: 1.44 (s, 6H); 1.66 (s, 6H); 1.72 (m, 4H); 4.74 (s, 2H); 6.47 (s, 1H); 7.08 to 7.62 (m, 12H); $^{13}$C NMR/THF: 31.5; 2*CH$_3$/34.4; 2*CH$_3$/37.4; Cq/37.9; Cq/38.2; CH$_2$/39.5; CH/70.7; CH$_2$/79.7; Cq/107.2; Cq/111.0; CH/113.5; Cq/128.0 to 129.1; 7*CH/133.3; Cq/136.4; Cq/136.5; Cq/136.6; Cq/136.8; Cq/146.4; Cq/158.5; Cq.

EXAMPLE 22

Ethyl 5-[5-Adamantan-1-yl-4-(2-methoxyethoxymethoxy)-2-methylphenylselenyl]-3-methylpent-2-en-4-ynoate a) 5-Adamantan-1-yl-4-(2-methoxyethoxymethoxy)-2-methylphenyl Diselenide A small portion of a solution of 2-(adamantan-1-yl)-4-bromo-5-methyl-l-methoxyethoxymethoxyphenyl (17 g, 41.5 mmol) in THF (160 ml) is poured into a mixture of magnesium (1.51 g) and a crystal of iodine, with gentle heating. When the reaction medium becomes uncoloured, the rest of the solution is added so as to maintain a slight reflux. After the end of the addition, the solution is refluxed for 1 h. After cooling to room temperature, 3.6 g of selenium are added. The reaction medium is stirred for 3 h at room temperature, followed by addition of 1N hydrochloric acid solution (105 ml) and ethyl ether. The organic phase is washed with water, dried over magnesium sulphate and concentrated on a rotary evaporator. Sodium hydroxide (131 mg) and ethanol (27 ml) are then added. The suspension is stirred in air at room temperature for 12 h. The product is isolated by filtration and the sodium hydroxide is removed by filtration through silica the dichloromethane. 12 g (71%) of a yellow solid are obtained. m.p.=101° C.

$^1$H NMR/CDCl$_3$: 1.73 (s, 6H); 2.00 (s, 9H); 2.30 (s, 3H); 3.40 (s, 3H); 3.59 (m, 2H); 3.83 (m, 2H); 5.29 (s, 2H); 6.95 (s, 1H); 7.48 (s, 1H).

b) Ethyl 5-[2-Adamantan-1-yl)-5-methyl-1-methoxyethoxymethoxyphen-4-ylselenyl)-3-methylpent-2-en-4-ynoate The product is obtained in a manner similar to that of Example 1(c). However, the addition of bromine takes place at 0° C. and the bromine/diselenide mixture is stirred for only 5 min before addition of the copper iodide, the DMF and the alkyne. Starting with 150 mg of ethyl 3-methylpent-2-en-4-ynoate (Example 1(b)) and 500 mg of the product obtained above, the expected compound is obtained in the form of a colourless oil.

$^1$H NMR/CDCl$_3$: 1.27 (s, 3H); 1.77 (s, 6H); 2.09 (s, 9H); 2.33 (s, 3H); 3.41 (s, 3H); 3.59 (m, 2H); 3.84 (m, 2H); 4.16 (q, 2H); 5.30 (s, 2H); 6.03 (s, 1H); 7.02 (s, 1H); 7.56 (s, 1H).

EXAMPLE 23

5-[5-Adamantan-1-yl-4-(2-methoxyethoxymethoxy)-2-methylphenylselenyl]-3-methylpent-2-en-4-ynoic Acid In a manner similar to that of Example 2, starting with the product of Example 22, the expected compound is obtained in the form of a white solid.

$^1$H NMR/CDCl$_3$: 1.76 (s, 6H); 2.09 (s, 9H); 2.34 (s, 3H); 3.40 (s, 3H); 3.60 (m, 2H); 3.84 (m, 2H); 5.30 (s, 2H); 6.03 (s, 1H); 7.03 (s, 1H); 7.55 (s, 1H).

EXAMPLE 24

5-[5-Adamantan-1-yl-4-(2-methoxyethoxymethoxy)-2-methylphenylselenyl]-3-propylpent-2-en-4-ynoic Acid The product is obtained in a manner similar to that of Example 22(b). Starting with 150 mg of 3-propylpent-2-en-4-ynoic acid (Example 19(c)) and 500 mg of 2-methyl-4-methoxyethoxymethoxy-5-(adamantan-1-yl) 1-diselenide, the expected compound is obtained in the form of a yellowish solid.

$^1$H NMR/CDCl$_3$: 0.90 (t, 3H); 1.64 (q, 2H); 1.27 (s, 3H); 1.77 (s, 6H); 2.09 (s, 9H); 2.34 (s, 3H); 2.78 (t, 2H); 3.41 (s, 3H); 3.60 (m, 2H); 3.85 (m, 2H); 5.30 (s, 2H); 6.03 (s, 1H); 7.03 (s, 1H); 7.54 (s, 1H).

EXAMPLE 25

5-[5-Adamantan-1-yl-4-(2-methoxyethoxymethoxy)-2-methylphenylselenyl]-3-phenylpent-2-en-4-ynoic Acid The product is obtained in a manner similar to that of Example 22(b). Starting with 168 mg of 3-phenylpent-2-en-4-ynoic acid (Example 16(c)) and 500 mg of 2-methyl-4-methoxyethoxymethoxy-5-(adamantan-1-yl) 1-diselenide, the expected compound is obtained in the form of a brown solid.

$^1$H NMR/CDCl$_3$: 1.71 (s, 6H); 1.98 (s, 9H); 2.31 (s, 3H) 3.40 (s, 3H); 3.59 (m, 2H); 3.83 (m, 2H); 5.29 (s; 2H); 6.22 (s, 1H); 7.00 (s, 1H); 7.29 to 7.46 (m, 6H).

EXAMPLE 26

Ethyl 5-(3,5-Di-tert-butyl-2-methoxymethoxyphenylselenyl)-3-methylpent-2-en-4-ynoate a) 2-Bromo-4,6-di-tert-butyl-1-methoxymethoxyphenyl In a manner similar to that of Example 20(b), starting with 2-bromo-4,6-di-tert-butylphenol, caesium carbonate and methoxymethyl chloride, the product is obtained in the form of an oil.

b) 4,6-Di-tert-butyl-1-methoxymethoxyphen-2-yl Diselenide

In a manner similar to that of Example 22(a), starting with 10 g of the product obtained above, 1.1 g of magnesium and 2.63 g of selenium, 7.6 g (76%) of the expected product are obtained in the form of a yellow solid.

$^1$H NMR/CDCl$_3$: 1.18 (s, 9H); 1.42 (s, 9H); 3.68 (s, 3H); 5.08 (s, 2H); 7.23 (d, 1H); 7.54 (d, 1H).

c) Ethyl 5-(3,5-Di-tert-butyl-2-methoxymethoxyphenylselenyl)-3-methylpent-2-en-4-ynoate In a manner similar to that of Example 22(b), starting with 617 mg of the product obtained above, 232 mg of ethyl 3-methylpent-2-en-4-ynoate, the expected product is obtained in the form of a colourless oil.

$^1$H NMR/CDCl$_3$: 1.28 (t, 3H); 1.32 (s, 9H); 1.40 (s, 9H); 2.37 (d, 3H); 3.67 (s, 3H); 4.18 (q, 2H); 5.01 (s, 2H); 7.29 (d, 1H); 7.63 (d, 1H).

EXAMPLE 27

5-(3,5-Di-tert-butyl-2-methoxymethoxyphenylselenyl)-3-methylpent-2-en-4-ynoic Acid In a manner similar to that of Example 2, starting with the product of Example 26, the expected compound is obtained in the form of a white solid.

$^1$H NMR/CDCl$_3$: 1.33 (s, 9H); 1.40 (s, 9H); 2.38 (d, 3H); 3.67 (s, 3H); 5.01 (s, 2H); 6.05 (d, 1H); 7.29 (d, 1H); 7.63 (d, 1H).

EXAMPLE 28

Ethyl 3-Methyl-5-(5,5,8,8-tetramethyl-3-hexyloxy-5,6,7,8-tetrahydronaphthalen-2-ylselenyl)pent-2-en-4-ynoate a) 4-Hexyloxy-5,6,7,8-tetrahydro-5,5,8,8-tetramethylnaphthalene 2-Diselenide 60% sodium hydride (225 mg, 5.63 mmol) is added portionwise to a solution of 4-hydroxy-5,6,7,8-tetrahydro- 5,5,8,8-tetramethylnaphthalene 2-diselenide (1.2 g, 2.56 mmol) in 15 ml of THF and 15 ml of THF. Stirring is continued for 30 min at room temperature after the end of the addition, and iodohexane (1 ml, 6.8 mmol) is added. The reaction medium is stirred for 4 h at room temperature and is then treated with water and ethyl ether. The organic phase is washed with water, dried over magnesium sulphate and concentrated. After purification by fast plug (95 heptane/5 $CH_2Cl_2$), the product is obtained in the form of a yellow oil.

$^1$H NMR/CDCl$_3$: 0.90 (m, 9H); 1.30 to 1.48 (m, 12H); 1.59 (m, 4H); 1.77 (m, 2H); 3.85 (t, 2H); 6.92 (d, 1H); 7.17 (d, 1H).

b) Ethyl 3-Methyl-5-(5,5,8,8-tetramethyl-3-hexyloxy-5,6,7,8-tetrahydronaphthalen-2-ylselenyl)pent-2-en-4-ynoate In a manner similar to that of Example 22(b), starting with 689 mg of the product obtained above and 232 mg of ethyl 3-methylpent-2-en-4-ynoate, the expected product is obtained in the form of a colourless oil.

$^1$H NMR/CDCl$_3$: 0.90 (m, 9H); 1.26 to 1.38 (m, 15H); 1.56 (m, 4H); 1.85 (m, 2H); 2.35 (s, 3H); 3.95 (t, 2H); 4.17 (q, 2H); 6.00 (d, 1H); 6.84 (d, 1H); 7.07 (d, 1H).

EXAMPLE 29

3-Methyl-5-(5,5,8,8-tetramethyl-3-hexyloxy-5,6,7,8-tetrahydronaphthalen-2-ylselen-yl)pent-2-en-4-ynoic Acid In a similar manner to that of Example 2, starting with 513 mg of the product of Example 27, the expected compound is obtained in the form of a white solid.

$^1$H NMR/CDCl$_3$: 0.90 (m, 9H); 1.30 (s, 12H); 1.38 (s, 12H); 1.59 (m, 4H); 1.85 (m, 2H); 2.35 (s, 3H); 3.95 (t, 2H); 6.02 (s, 1H); 6.83 (d, 1H); 7.08 (d, 1H).

EXAMPLE 30

5-[4-Adamantan-1-yl-3-(2-methoxyethoxymethoxy)phenylselenyl]-3-propylpent-2-en-4-ynoic Acid a) 2-(Adamantan-1-yl)-5-bromo-1-(2-methoxyethoxymethoxy)phenyl In a similar manner.to that of Example 28(a), starting with 20.9 g of 2-(adamantan-1-yl)-5-bromo-1-phenol, 2.5 g of sodium hydride and 8.92 g of methoxyethoxymethyl chloride, 17 g (64%) of the expected product are obtained in the form of a white solid. m.p.=88° C.

b) 4-Adamantan-1-yl-3-(2-methoxyethoxymethoxy)phenyl Diselenide

In a manner similar to that of Example 1(a), starting with 13.04 g of 2-(adamantan-1-yl)-5-bromo-1-methoxyethoxymethoxyphenyl, 9.9 g (76%) of the expected product are obtained in the form of a yellow oil.

$^1$H NMR/CDCl$_3$: 1.55 (s, 6H); 2.05 (d, 9H); 3.38 (s, 3H); 3.57 (m, 2H); 3.82 (m, 2H); 5.27 (s, 2H); 7.11 (d, 1H); 7.22 (dd, 1H); 7.38 (d, 1H).

c) 5-[4-Adamantan-1-yl-3-(2-methoxyethoxymethoxy)phenylselenyl]-3-propylpent-2-en-4-ynoic Acid In a manner similar to that of Example 22(b), tarting with 600 mg of the product obtained above and 202 mg of 3-propylpent-2-en-4-ynoic acid (Example 19(c)), the expected product is obtained in the form of a white solid. m.p.=95° C.

$^1$H NMR/CDCl$_3$: 0.97 (t, 3H); 1.66 (q, 2H); 1.76 (s, 6H); 2.07 (s, 9H); 2.80 (t, 2H); 3.38 (s, 3H); 3.61 (m, 2H); 3.85 (m, 2H); 5.33 (s, 2H); 6.12 (s, 1H); 7.08 to 7.35 (m, 3H); $^3$C NMR/CDCl$_3$: 13.7; CH$_3$/21.9; CH$_2$/29.0; CH/34.0; CH$_2$/37.0; CH$_2$/40.6; CH$_2$/59.0; CH$_3$/67.8; CH$_2$/71.6; CH$_2$/79.1; Cq/93.4; CH$_2$/107; Cq/115.2; CH/122.2; CH/125.8; 2*Cq/127.9; CH/13.3; 2*Cq/157.3; Cq.

EXAMPLE 31

Ethyl 5-[2-(Adamantan-1-yl)-1-methoxyethoxymethoxyphen-5-ylselenyl)-3-methylpent-2-en-4-ynoate In a manner similar to that of Example 22 (b), starting with 600 mg of the product of Example 30(b) and 202 mg of ethyl 3-methylpent-2-en-4-ynoate (Example 1(b)), 300 mg (74%) of the expected product are obtained in the form of a brown oil.

$^1$H NMR/CDCl$_3$: 1.28 (t, 3H); 1.76 (s, 6H); 2.05 (m, 9H); 2.37 (s, 3H); 3.39 (s, 3H); 3.60 (m, 2H); 3.85 (m, 2H); 4.17 (q, 2H); 5.30 (s, 3H); 6.04 (d, 1H); 7.09 to 7.32 (m, 3H).

EXAMPLE 32

Ethyl 5-[4-(2-Methoxyethoxymethoxy)-5,5,8,8-tetramethyl-5,6,7,8-tetrahydronaphthalen-2-ylsulphonyl]-3-methylpent-2-en-4-ynoate a) 5-(2-Methoxyethoxymethoxy)-7-thiol-1,1,4,4-tetramethyl-1,2,3,4-tetrahydronaphthalene A 1.7 M solution of tert-butyllithium in pentane (95 mmol, 56 ml) is added to a solution of 7-bromo-5-(2-methoxyethoxymethoxy)-,1,4,4-tetramethyl-1,2,3,4-tetrahydronaphthalene (16.02 g, 43 mmol) in THF (300 ml) at −78° C. over 10 min. The mixture is stirred at 0° C. for 30 min. Sulphur (1.49 g, 46 mmol) is added in 2 portions at −70° C. The mixture is stirred for 2.5 h. 2N HCl solution is added and the reaction mixture is then treated with ethyl ether. The organic phase is washed twice with water, dried over anhydrous magnesium sulphate and concentrated on a rotary evaporator under vacuum at 40° C. The product is purified by flash chromatography (9 heptane/1 EtOAc).

Yellow oil. Mass: 3.73 g. Yield: 29%.

b) 7-(2,2-Dichlorovinylsulphonyl)-5-(2-methoxyethoxymethoxy)-1,1,4,4-tetramethyl-1,2,3,4-tetrahydronaphthalene In a manner similar to that of Example 5(a), starting with 1.3 g of 5-(2-methoxyethoxymethoxy)-7-thiol-1,1,4,4-tetramethyl-1,2,3,4-tetrahydronapthalene, 688 mg of 35% potassium hydride and 431 µl of trichloroethylene, 1.27 g (76%) of the expected product are obtained in the form of a yellow oil.

c) 7-Ethynylsulphonyl-5-(2-methoxyethoxymethoxy)-1,1,4,4-tetramethyl-1,2,3,4-tetrahydronaphthalene In a manner similar to that of Example 5(b), starting with 625 mg of the product obtained above and 1.3 ml of n-butyllithium solution (2.5M/hexane), 410 mg (67%) of the expected product are obtained in the form of a yellow oil.

d) Ethyl 5-[4-(2-Methoxyethoxymethoxy)-5,5,8,8-tetramethyl-5,6,7,8-tetrahydronaphthalen-2-ylsulphonyl]-3-methylpent-2-en-4-ynoate In a manner similar to that of Example 5(c), starting with 613 mg of the product obtained above and 471 mg of ethyl butynoate, 162 mg (20%) of the expected E isomer in the form of a yellow oil and 59 mg (7%) of the Z isomer in the form of a yellow oil are obtained.

$^1$H NMR/CDCl$_3$: E isomer: 1.27 (s, 6H), 1.26 to 1.28 (t, 3H), 1.37 (s, 6H), 1.60 to 1.65 (m, 4H), 2.37 (d, 3H), 3.39 (s, 3H), 3.58 (t, 2H), 3.82 (t, 2H), 4.13 to 4.21 (q, 2H), 5.29 (s, 2H), 6.02 (d, 1H), 7.06 (d, 1H), 7.10 (d, 1H); Z isomer: 1.25 (s, 6H), 1.20 to 1.25 (t, 3H), 1.35 (s, 6H), 1.63 to 1.65 (m, 4H), 2.40 (d, 3H), 3.38 (s, 3H), 3.58 (t, 2H), 3.82 (t, 2H), 4.09 to 4.12 (q, 2H), 5.28 (s, 2H), 5.44 (d, 1H), 7.08 (d, 1H), 7.11 (d, 1H).

EXAMPLE 33

(Z)-5-[4-(2-Methoxyethoxymethoxy)-5,5,8,8-tetramethyl-5,6,7,8-tetrahydronaphthalen-2-ylsulphonyl]-3-methylpent-2-en-4-ynoic Acid In a manner similar to that of Example 2, starting with 56 mg of the Z isomer of Example 32, 25 mg (48%) of the expected compound are obtained.

¹H NMR/CDCl₃: 1.25 (s, 6H), 1.39 (s, 6H), 1.60 to 1.68 (m, 4H), 2.41 (s, 3H), 3.37 (s, 3H), 3.57 (t, 2H), 3.81 (t, 2H), 5.28 (s, 2H), 5.35 (m, 1H), 7.1 (d, 2H).

EXAMPLE 34

(E)-5-[4-(2-Methoxyethoxymethoxy)-5,5,8,8-tetramethyl-5,6,7,8-tetrahydronaphthalen-2-ylsulphonyl]-3-methylpent-2-en-4-ynoic Acid In a manner similar to that of Example 2, starting with 155 mg of the E isomer of Example 32, 45 mg (32%) of the expected compound are obtained.

¹H NMR/CDCl₃: 1.26 (s, 6H), 1.37 (s, 6H), 1.60 to 1.67 (m, 4H), 2.38 (d, 3H), 3.39 (s, 3H), 3.61 (t, 2H), 3.84 (t, 2H), 5.30 (s, 2H), 6.10 (d, 1H), 7.3 (d, 1H), 7.15 (d, 1H).

EXAMPLE 35

Methyl 5-(3,5,5,8,8-Pentamethyl-5,6,7,8-tetrahydronaphthalen-2-ylsulphonyl)penta-2,4-diynoate A 70% solution of ethylamine in water (563 μl) is added dropwise to a mixture of methyl 3-bromopropynoate (632 mg, 2.88 mmol), hydroxylamine hydrochloride (162 mg, 2.33 mmol) and copper (I) chloride (10 mg) in methanol. A solution of 6-ethynylsulphonyl-1,1,4,4,7-pentamethyl-1,2,3,4-tetrahydronaphthalene (Example 7(b)) (500 mg, 1.94 mmol) in methanol (5 ml) is then added dropwise. The reaction medium is stirred for 15 h at room temperature and treated with saturated aqueous ammonium chloride solution and ethyl acetate. The organic phase is washed with water, dried over magnesium sulphate and concentrated. The product is obtained in the form of an oil after purification by flash chromatography on silica (80/20 heptane/CH₂Cl₂). ¹H NMR/CDCl₃: 1.26 to 1.28 (s, 12H); 1.67 (s, 4H); 2.35 (s, 3H); 3.78 (s, 3H); 7.14 (s, 1H); 7.48 (s, 1H); ¹³C NMR/CDCl₃: 19.7; CH₃/31.8; 4*CH₃/34.1; Cq/34.3; Cq/34.9; 2*CH₂/52.9; CH₃/71.7; CH/72.1; CH/80.2; Cq/124.5; Cq/127.6; Cq/12.8.3; CH/129.3; CH/134.8; Cq/144.6; Cq/146.2; Cq/153.4; Cq.

EXAMPLE 36

Ethyl 5-(3-Benzyloxy-5,5,8,8-tetramethyl-5,6,7,8-tetrahydronaphthalen-2-ylselenyl)-3-methylpent-2-en-4-ynoate a) 3-Benzyloxy-5,6,7,8-tetrahydro-5,5,8,8-tetramethylnaphthalene 2-Diselenide In a manner similar to that of Example 20(b), the expected product is obtained by the action of caesium carbonate on 3-hydroxy-5,6,7,8-tetrahydro-5,5,8,8-tetramethylnaphthalene 2-diselenide (Example 15(b)).

c) Ethyl 5-(3-Benzyloxy-5,5,8,8-tetramethyl-5,6,7,8-tetrahydronaphthalen-2-ylselenyl)-3-methylpent-2-en-4-ynoate The expected product is obtained in a manner similar to that of Example 22(b), with introduction of bromine carried out at −70° C. 650 mg (71%) of a yellowish powder are obtained.

¹H NMR/CDCl₃: 1.23 (s, 6H), 1.26 to 1.32 (s, t, 9H), 1.67 (s, 4H), 2.40 (d, 3H), 4.14 to 4.22 (q, 2H), 5.10 (s, 2H), 6.06 (d, 1H), 6.78 (s, 1H), 7.32 to 7.44 (m, 5H), 7.57 (s, 1H).

EXAMPLE 37

5-(3-Benzyloxy-5,5,8,8-tetramethyl-5,6,7,8-tetrahydronaphthalen-2-ylselenyl)-3-methylpent-2-en-4-ynoic Acid In a manner similar to that of Example 2, starting with 630 mg of the product of Example 36, the expected compound is obtained in the form of a yellowish powder.

¹H NMR/CDCl₃: 1.23 (s, 6H), 1.29 (s, 6H), 1.67 (s, 4H), 2.42 (d, 3H), 5.11 (s, 2H), 6.08 (d, 1H), 6.79 (s, 1H), 7.32 to 7.44 (m, 5H), 7.56 (s, 1H).

EXAMPLE 38

Ethyl 5-[3-(2-methoxyethoxymethoxy)-5,5,8,8-tetramethyl-5,6,7,8-tetrahydronaphthalen-2-ylselenyl]-3-methylpent-2-en-4-ynoate a) 3-(2-Methoxyethoxymethoxy)-5,6,7,8-tetrahydro-5,5,8,8-tetramethylnaphthalene 2-Diselenide In a manner similar to that of Example 28(a), the expected product is obtained by the action of sodium hydride on 3-hydroxy-5,6,7,8-tetrahydro-5,5,8,8-tetramethylnaphthalene 2-diselenide (Example 15b).

b) Ethyl 5-[3-(2-Methoxyethoxymethoxy)-5,5,8,8-8-tetramethyl-5,6,7,8-tetrahydronaphthalen-2-ylselenyl]-3-methylpent-2-en-4-ynoate The expected product is obtained in a manner similar to that of Example 22(b), with introduction of the bromine carried out at −70° C. 705 mg (77%) of a yellow oil are obtained.

¹H NMR/CDCl₃: 1.27 (s, 6H), 1.25 to 1.28 (t, 3H), 1.37 (s, 6H), 1.62 to 1.63 (m, 4H), 2.35 (d, 3H), 3.39 (s, 3H), 3.58 (t, 2H), 3.83 (t, 2H), 4.13 to 4.21 (q, 2H), 5.29 (s, 2H), 6.03 (d, 1H), 7.16 (s, 2H).

EXAMPLE 39

5-[3-(2-Methoxyethoxymethoxy)-5,5,8,8-tetramethyl-5,6,7,8-tetrahydronaphthalen-2-ylselenyl]-3-methylpent-2-en-4-ynoic Acid In a manner similar to that of Example 2, starting with 693 mg of the product of Example 38, the expected compound is obtained in the form of a yellowish oil.

¹H NMR/CDCl₃: 1.27 (s, 6H), 1.37 (s, 6H), 1.62 to 1.63 (m, 4H), 2.36 (d, 3H), 3.39 (s, 3H), 3.60 (t, 2H), 3.84 (t, 2H), 5.30 (s, 2H), 6.09 (d, 1H), 7.14 (d, 1H), 7.19 (d, 1H).

EXAMPLE 40

Methyl 5-(3,5,5,8,8-Pentamethyl-5,6,7,8-tetrahydronaphthalen-2-ylselenyl)penta-2,4-diynoate a) 6-Trimethylsilylethynylselenyl-1,1,4,4-tetramethyl-1,2,3,4-tetrahydronaphthalene In a manner similar to that of Example 1(c), the product is obtained by coupling trimethylsilylacetylene (2.4 ml, 17.2 mmol) and 1 g (1.79 mmol) of 5,6,7,8-tetrahydro-3,5,5,8,8-pentamethylnaphthalene 2-diselenide (Example 3(a)) at room temperature in DMF catalysed with CuI (1 g).

¹H NMR/CDCl₃: 0.10 (s, 9H); 1.10 (d, 12H); 1.48 (s, 4H); 2.09 (s, 3H); 6.90 (s, 1H); 7.54 (s, 1H).

b) 6-Ethynylselenyl-1,1,4,4-tetramethyl-1,2,3,4-tetrahydronaphthalene

In a manner similar to that of Example 1(b), the product is obtained by the action of 1 g of caesium fluoride on 6-trimethylsilylethynylselenyl-1,1,4,4-tetramethyl-1,2,3,4-tetrahydronaphthalene (500 mg, 3.6 mmol) at room temperature in a mixture of methanol and THF for 24 h.

¹H NMR/CDCl₃: 1.25 (d, 12H); 1.65 (s, 4H); 2.33 (s, 3H) 3.11 (s, 1H); 7.10 (s, 1H); 7.68 (s, 1H); ¹³C NMR/CDCl₃: 31.8; 4*CH₃/34.0; Cq/34.3; Cq/35.0; 2*CH₂/73.1; Cq/90.7; CH/124.5; Cq/128.5; CH/128.9; CH/134.5; Cq/144.6; Cq/144.9; Cq.

d) Methyl 5-(3,5,5,8,8-Pentamethyl-5,6,7,8-tetrahydronaphthalen-2-ylselenyl)penta-2,4-diynoate In a manner similar to that of Example 35, the expected product is obtained by coupling 321 mg of methyl bromopropynoate and 200 mg of 6-ethynylselenyl-1,1,4,4-tetramethyl-1,2,3,4-tetrahydronaphthalene, in a yield of 28% (70 mg).

$^1$H NMR/CDCl$_3$: 1.23 (s, 6H); 1.33 (s, 6H); 1.67 (s, 4H); 2.35 (s, 3H); 3.79 (s, 3H); 7.13 (s, 1H); 7.65 (s, 1H).

EXAMPLE 41

Ethyl 5-(4-Benzyloxy-5,5,8,8-tetramethyl-5,6,7,8-tetrahydronaphthalen- 2-ylselenyl)-3-methylpent-2-en-4-ynoate In a manner similar to that of Example 22(b), with introduction of bromine carried out at −70° C., the expected product is obtained by coupling 464 mg of 4-benzyloxy-5,6,7,8-tetrahydro-5,5,8,8-tetramethylnaphthalene 2-diselenide (Example 21(b)) and 300 mg of ethyl 3-methylpent-2-en-4-ynoate, in a yield of 65% (300 mg).

$^1$H NMR/CDCl$_3$: 1.28 (m, 9H); 1.38 (s, 6H); 1.63 (m, 4H); 2.33 (d, 3H); 4.17 (q, 2H); 5.08 (s, 2H); 6.00 (t, 1H); 6.93 (d, 1H); 7.11 (d, 1H); 7.31 to 7.47 (m, 5H); $^{13}$C NMR/CDCl$_3$: 14.6; CH$_3$/28.8; 2*CH$_3$/32.3; 2*CH$_3$/34.7; CH$_2$/35.2; Cq/35.5; CH$_2$/38.3; Cq/60.4; CH$_2$/70.9; CH$_2$/78.0; Cq/105.9; Cq/110.9; CH/121.1; CH/123.0; Cq/125.5; Cq/128.0 5*CH/128.3; CH/129.0; 4*CH/133.5; Cq/137.2; Cq/137.7; Cq/149.4; Cq/159.0; Cq/166.5; Cq.

EXAMPLE 42

Ethyl 5-[3-5-(tert-Butyldimethylsilanyloxy) pentyloxymethyl]-5,5,8,8-tetramethyl-5,6,7,8-tetrahydronaphthalen-2-ylselenyl]-3-methylpent-2-en-4-ynoate a) 5-(3-Bromo-5,5,8,8-tetramethyl-5,6,7,8-tetrahydronaphthalen-2-yloxy)pentyl Acetate A solution of 3-bromo-5,5,8,8-tetramethyl-5,6,7,8-tetrahydronaphthalen-2-ol (10 g, 0.35 mol), 5-bromopentyl acetate (8.15 g) and potassium carbonate (33.6 g) in methyl ethyl ketone (200 ml) is refluxed for 2 hours. The reaction medium is treated with water and ethyl acetate. After separation of the phases by settling, the organic phase is washed twice with water, dried over magnesium sulphate and concentrated on a rotary evaporator under vacuum at 40° C. The product is purified by flash chromatography on a column of silica.

Yellow oil. Yield: 93%.

b) [5-(3-Bromo-5,5,8,8-tetramethyl-5,6,7,8-tetrahydronaphthalen-2-yloxy)pentyloxy]tert-butyldimethylsilane The acetate obtained above is saponified and the resulting hydroxyl group is then protected according to the following procedure: tert-Butyldimethylsilyl chloride (2.64 g) is added to a mixture of 5-(3-bromo-5,5,8,8-tetramethyl-5,6,7,8-tetrahydronaphthalen-2-yloxy)pentan-1-ol (4.3 g, 11.7 mmol) and 80% sodium hydride (422 mg) in THF (20 ml). The mixture is stirred at room temperature for 2 h. The solution is poured into a mixture of water and ethyl acetate. The organic phase is washed twice with water, dried over magnesium sulphate and concentrated on a rotary evaporator under vacuum at 40° C. The product is purified by flash chromatography on a column of silica.

Yellow oil. Yield: 64%.

c) 3-[5-(tert-Butyldimethylsilanyloxy)pentyloxymethyl]-5,5,8,8-tetramethyl-5,6,7,8-tetrahydronaphthalene 2-Diselenide The expected product is obtained from the bromo derivative obtained above, in a manner similar to that of Example 1(a). Yellow oil. Yield: 10%.

d) Ethyl 5-[3-[5-(tert-Butyldimethylsilanyloxy) pentyloxymethyl]-5,5,8,8-tetramethyl-5,6,7,8-tetrahydronaphthalen-2-ylselenyl]-3-methylpent-2-en-4-ynoate The product obtained above is coupled with ethyl 3-methylpent-2-en-4-ynoate according to the procedure of Example 1(c), to give the expected product in the form of a colourless oil. Yield: 12%.

$^1$H NMR/CDCl$_3$: 0.00 (s, 6H); 0.84 (s, 9H); 1.21 to 1.27 (m, 15H); 1.46 to 1.52 (m, 4H); 1.62 (s, 4H); 1.73 (m, 2H); 2.35 (d, 3H); 3.41 (t, 2H); 3.95 (t, 2H); 4.13 (q, 2H); 6.00 (d, 1H); 6.66 (s, 1H); 7.48 (s, 1H).

EXAMPLE 43

5-[3-[5-(tert-Butyldimethylsilanyloxy) pentyloxymethyl]- 5,5,8,8-tetramethyl-5,6,7,8-tetrahydronaphthalen-2-ylselenyl]-3-methylpent-2-en-4-ynoic Acid The product of Example 42 is saponified according to the procedure of Example 2 to give the expected product in the form of a yellowish solid.

$^1$H NMR/CDCl$_3$: 0.00 (s, 6H); 0.84 (s, 9H); 1.21 (s, 6H); 1.23 (s, 6H); 1.46 to 1.51 (m, 4H); 1.60 (s, 4H); 1.72 to 1.77 (m, 2H); 2.36 (d, 3H); 3.58 (t, 2H); 3.95 (t, 2H); 6.02 (d, 1H); 6.66 (s, 1H); 7.48 (s, 1H).

EXAMPLE 44

Ethyl 5-[3-(5-Hydroxypentyloxy)-5,5,8,8-tetramethyl-5,6,7,8-tetrahydronaphthalen-2-ylselenyl]-3-methylpent-2-en-4-ynoate A mixture of the product of Example 43 (105 mg, 177 µmol), a 1M 1HF solution of tetra-n-butylammonium fluoride (770 µl) in THF is stirred at room temperature for 6 h. The reaction medium is treated with 1N HCl solution and ethyl ether. After separation of the phases by settling, the organic phase is washed with water, dried over anhydrous magnesium sulphate and concentrated. The product is purified by crystallization from a mixture of heptane and ethyl ether. Mass: 48 mg, yellowish powder. m.p.=134° C. $^1$H NMR/CDCl$_3$: 1.18 to 1.29 (m, 14H); 1.56 to 1.68 (m, 8H); 1.83 (m, 2H); 2.42 (d, 3H); 3.69 (t, 2H); 4.02 (t, 2H); 6.08 (d, 1H); 6.72 (s, 1H); 7.54 (s, 1H).

EXAMPLE 45

5-(4-Fluoro-3-methylphenylselenyl)-3-methylpent-2-en-4-ynoic Acid a) Preparation of the Resin A mixture of 3-methylpent-2-en-4-ynoic acid (Example 20(c)) (12.6 mmol, 1.51 g), caesium carbonate (16.8 =mol, 3.24 g) and 4 g of Wang-bromo polystyrene resin (Novabiochem ref. 01-64-0186) in 30 ml of DMF is heated at 60° C. for 24 h. The mixture is filtered and then washed three times with DMF, water, THF, methanol and dichloromethane.

b) $^4$-Fluoro-3-methylphenyl Diselenide

The expected product is synthesized according to the procedure of Example 22 (a).

c) 4-Fluoro-3-methylphenylselenyl Bromide.

Bromine (0.048 ml, 0.93 mmol) is added to a solution of 4-fluoro-3-methylphenyl diselenide (0.94 mmol) in THF (1 ml). The mixture is stirred at room temperature for 2 h and the solvent is then removed with a strong stream of nitrogen.

d) 5-(4-Fluoro-3-methylphenylselenyl)-3-methylpent-2-en-4-ynoic Acid

A mixture of the resin obtained above (1 g, 1.04 mmol), 4-fluoro-3-methylphenylselenyl bromide (2.5 mmol), CuI (I) (5 mmol) and tributylamine (4 mmol) is stirred at 60° C. for 24 h. The resin is filtered and then washed three times with DMF, water, THF and dichloromethane. The product is obtained after cleavage with 10% trifluoroacetic acid solution for 7 min.

$^1$H NMR/CDCl$_3$: 2.29 (d, 3H); 2.31 (d, 3H); 6.05 (d, 1H) 7.13 (d, 1H); 7.47 to 7.54 (m, 2H).

EXAMPLE 46

3-Methyl-5-p-tolylselenylpen-2-en-4-ynoic Acid

The expected product is obtained according to the same procedure as that of Example 45.

$^1$H NMR/CDCl$_3$: 2.34 (s, 3H); 6.04 (s, 1H); 7.16 (d, 2H); 7.42 (d, 2H).

EXAMPLE 47

5-(6-Bromo-4,4-dimethylthiochroman-8-ylselenyl)-3-methylpent-2-en-4-ynoic Acid a) 2-Bromo-1-(3-methylbut-2-enylthio)benzene 19.30 g (102.0 mmol) of 2-bromothiophenol, 160 ml of DMF and 15.50 g (112.0 mmol) of potassium carbonate are introduced into a three-necked flask. 13 ml (112.0 mmol) of 1-bromo-3-methyl-2-butene are added dropwise and the mixture is stirred at room temperature for two hours. The reaction medium is poured into water and extracted with ethyl acetate, and the organic phase is separated out after settling, washed with water, dried over magnesium sulphate and evaporated. 26.00 g (99%) of the expected compound are collected in the form of an orange-coloured oil.

$^1$H NMR(CDCl$_3$): δ 1.65 (s, 3H), 1.73 (s, 3H), 3.56 (d, 2H, J=7.7 Hz), 5.32 (td, 1H, J=7.7/1.4 Hz), 6.96 to 7.06 (m, 1H), 7.22 to 7.26 (m, 2H), 7.52 (d, 1H, J=7.7 Hz).

b) 4,4-Dimethyl-8-bromothiochroman 26.00 g (102.0 mmol) of 2-bromo-1-(3-methylbut-2-enylthio)benzene, 180 ml of toluene and 23.20 g (122.0 mmol) of para-toluenesulphonic acid are introduced into a three-necked flask. The reaction medium is refluxed for four hours and is then evaporated to dryness. The residue is taken up in aqueous sodium hydrogen carbonate solution and extracted with ethyl acetate, and the organic phase is separated out after settling, dried over magnesium sulphate and evaporated The residue obtained is purified by chromatography on a column of silica and eluted with heptane. 20 g (76%) of the expected compound are collected in the form of an orange-coloured oil.

$^1$H NMR(CDCl$_3$) δ 1.33 (s, 6H), 1.94 (t, 2H, J=6.0 Hz), 3.04 (t, 2H, J=6.1 Hz), 6.89 (t, 1H, J=7.9 Hz), 7.34 (d, 2H, J=7.9 Hz).

c) 4,4-Dimethylthiochroman 8-Diselenide

One crystal of iodine, magnesium (208 mg, 8.56 mmol) and a few drops of a solution of 4,4-dimethyl-8-bromothiochroman (2 g, 7.78 mmol) in ethyl ether (15 ml) are heated until initiation of the organomagnesium reagent has taken place. The rest of the solution is then added dropwise. The reaction medium is heated for 2 h and selenium (615 mg, 7.78 mmol) is then added at room temperature. Stirring is continued for 30 min and 1N HCl solution is then added. The reaction mixture is treated with ethyl ether. The organic phase is washed twice with water, dried over anhydrous magnesium sulphate and concentrated on a rotary evaporator under vacuum at 40° C. Ethanol and sodium hydroxide are added to the oil obtained. The mixture is stirred vigorously for a few minutes and is then concentrated on a rotary evaporator under vacuum at 40° C.

The product is purified on a column of silica (20 dichloromethane/80 heptane). White solid. Mass: 300 mg. Yield: 15%.

$^1$H NMR(CDCl$_3$): 1.33 (6H, s), 1.96 (2H, m), 3.09 (2H, m), 6.93 (1H Ar, t, J=7.8 Hz), 7.26 (1H Ar, dd, J=7.8 Hz, J=1.3 Hz), 7.47 (1H Ar, dd, J=7.8 Hz, J=1.3 Hz).

d) 5-(6-Bromo-4,4-dimethylthiochroman-8-ylselenyl)-3-methylpent-2-en-4-ynoic Acid The procedure is identical to the one followed in Example 45, using the selenide obtained above.

$^1$H NMR(CDCl$_3$): 1.34 (6H, s), 1.96 (2H, m), 2.40 (3H, s), 3.13 (2H, m), 6.13 (1H, s), 7.43 (1H Ar, d), 7.64 (1H Ar, d).

EXAMPLE 48

This example illustrates several results of biological tests on examples of compounds of the invention.

| BIOLOGICAL ACTIVITY | | |
|---|---|---|
| Product | IC$_{50}$ (Nm)[a] | % of inhibition[b] |
| EXAMPLE 10 | 671 | 57% |
| EXAMPLE 12 | 71 | 92% |
| EXAMPLE 14 | 471 | 61% |

[a]Determination of the IC$_{50}$ values of the antagonist compounds

The antagonist activity can also be characterized in this system of cotransfection by determining the dose required to achieve 50% inhibition of the agonist activity obtained with 3 nM 6-[1-(3,5,5,8,8-pentamethyl-5,6,7,8-tetrahydro-2-naphthalenyl)cyclopropyl]nicotinic acid (IC$_{50}$). The product is thus tested at 5 different concentrations ranging from 10$^{-5}$ to 10$^{-9}$ M final in the presence of the agonist 6-[1-(3,5,5,8, 8-pentamethyl-5,6,7,8-tetrahydro 2-naphthalenyl) cyclopropyl]nicotinic acid at 3 nM. The dose-response curve obtained makes it possible to determine the IC$_{50}$ value which is specific to the compound.

b) Test of RXR Antagonist Transactivation

The properties of inhibition of the activation of the RXR response elements (RXRE) can be determined by recognized methods of the art.

The receptor expression plasmid pSG5-RXRalpha and the reporter plasmid CRBPII-tk-Luc are introduced into the Cos7 monkey kidney cell line by the method of coprecipitation with calcium phosphate described in Molecular Cloning: A laboratory manual (Sambrook et al. eds. Cold Spring Harbor Lab. Publ. 1989). 18 hours later, the cells are rinsed with PBS and are placed in DMEM medium free of phenol red (Gibco-BRL) containing 10% of defatted serum (Jacques Boy) and 3 nm of the reference agonist 6-[1-(3,5, 5,8,8-pentamethyl-5,6,7,8-tetrahydro-2-naphthalenyl) cyclopropyl]nicotinic acid. The test compound is added at 10$^{-6}$M final. After treatment for 18 h, the cells are rinsed with PBS and lysed in 0.1M KPO$_4$ (pH 7.8), 1.0% Triton X100, 1.0 mM DTT, 1 mM EDTA. The luciferase activity of the cell lysates is measured as described by deWet et al. in Mol. Cell. Biol. 7:725 (1987). The results are expressed as a percentage of inhibition of the induction obtained with the agonist 6-[1-(3,5,5,8,8-pentamethyl-5,6,7,8-tetrahydro-2-naphthalenyl)cyclopropyl]nicotinic acid alone.

The results presented above show the RXR-antagonist activity of several examples of compounds of the invention.

EXAMPLE 49

Various concrete formulations based on compounds according to the invention are illustrated in this example.

| A - ORAL ROUTE | |
| --- | --- |
| (a) 0.2 g tablet | |
| Compound of Example 1 | 0.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |
| (b) Drinkable suspension in 5 ml ampules | |
| Compound of Example 3 | 0.001 g |
| Glycerol | 0.500 g |
| 70% sorbitol | 0.500 g |
| Sodium saccharinate | 0.010 g |
| Methyl para-hydroxybenzoate | 0.040 g |
| Flavouring qs | |
| Purified water qs | 5 ml |
| (c) 0.8 g tablet | |
| Compound of Example 15 | 0.500 g |
| Pregelatinized starch | 0.100 g |
| Microcrystalline cellulose | 0.115 g |
| Lactose | 0.075 g |
| Magnesium stearate | 0.010 g |
| (d) Drinkable suspension in 10 ml ampules | |
| Compound of Example 36 | 0.05 g |
| Glycerol | 1.000 g |
| 70% sorbitol | 1.000 g |
| Sodium saccharinate | 0.010 g |
| Methyl para-hydroxybenzoate | 0.080 g |
| Flavouring qs | |
| Purified water qs | 10 ml |

| B - TOPICAL ROUTE | |
| --- | --- |
| (a) Ointment | |
| Compound of Example 27 | 0.020 g |
| Isopropyl myristate | 81.700 g |
| Liquid petroleum jelly | 9.100 g |
| Silica ("Aerosil 200" sold by Degussa) | 9.180 g |
| (b) Ointment | |
| Compound of Example 8 | 0.300 g |
| White petroleum jelly codex | 100 g |
| (c) Nonionic water-in-oil cream | |
| Compound of Example 41 | 0.100 g |
| Mixture of emulsifying lanolin alcohols, waxes and oils ("anhydrous Eucerin" sold by BDF) | 39.900 g |
| Methyl para-hydroxybenzoate | 0.075 g |
| Propyl para-hydroxybenzoate | 0.075 g |
| Sterile demineralized water qs | 100 g |
| (d) Lotion | |
| Compound of Example 6 | 0.100 g |
| Polyethylene glycol (PEG 400) | 69.900 g |
| 95% ethanol | 30.000 g |
| (e) Hydrophobic ointment | |
| Compound of Example 19 | 0.300 g |
| Isopropyl myristate | 36.400 g |
| Silicone oil ("Rhodorsil 47 V 300" sold by Rhône-Poulenc) | 36.400 g |
| Beeswax | 13.600 g |
| Silicone oil ("Abil 300,000 cst" sold by Goldschmidt) | 100 g |

-continued

| B - TOPICAL ROUTE | |
| --- | --- |
| (f) Nonionic oil-in-water cream | |
| Compound of Example 4 | 0.500 g |
| Cetyl alcohol | 4.000 g |
| Glyceryl monostearate | 2.500 g |
| PEG-50 stearate | 2.500 g |
| Karite butter | 9.200 g |
| Propylene glycol | 2.000 g |
| Methyl para-hydroxybenzoate | 0.075 g |
| Propyl para-hydroxybenzoate | 0.075 g |
| Sterile demineralized water | 100 g |

What is claimed is:

1. Heteroethynylenic compounds, corresponding to formula (I) below:

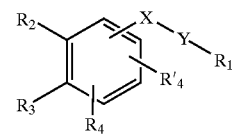

in which:

$R_1$ represents: (i) a —$CH_3$ radical
   (ii) a radical —$CH_2$—O—$R_5$
   (iii) radical —$COR_6$ $R_5$ and $R_6$ having the meanings given below, X represents: O, Se, S(O)n, n being 0, 1 or 2, Y represents a divalent radical which has the formula:

a)

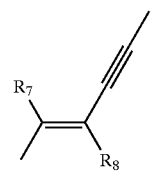

b)

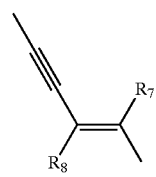

c)

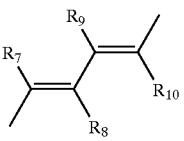

d)

$R_7$, $R_8$, $R_9$ and $R_{10}$ having the meanings given below, $R_2$ and $R_3$, taken together, form, with the adjacent aromatic ring, a 5- or 6-membered ring optionally substituted with methyl groups and/or optionally interrupted by an oxygen or sulphur atom, or $R_2$ and $R_3$ independently, which may be identical or different, can represent:

a) a hydrogen atom,
b) a radical comprising
   tert-butyl,
   1-methylcyclohexyl, or
   1-adamantyl,
c) a radical —OR$_{11}$
d) a polyether radical
e) a halogen atom
R$_{11}$ having the meaning given below, it being understood that at least one of the substituents R$_2$ and R$_3$ represents (b),
R$_4$ represents a hydrogen atom, a lower alkyl radical, a radical OR$_{12}$, a polyether radical, a radical COR$_{13}$ or a halogen atom,
R$_{12}$ and R$_{13}$ having the meanings given below,
R'$_4$ represents a hydrogen atom or a halogen atom,
R$_5$ represents a hydrogen atom or a lower alkyl radical,
R$_6$ represents:
  (i) a hydrogen atom
  (ii) a lower alkyl radical
  (iii) a radical OR$_{14}$
  R$_{14}$ having the meaning given below,
  (iv) a radical of formula

R' and R" having the meanings given below,
R$_7$, R$_8$, R$_9$ and R$_{10}$, which may be identical or different, represent a hydrogen atom, a lower alkyl radical or an aryl radical,
R$_{11}$ and R$_{12}$, which may be identical or different, represent a hydrogen atom, a lower alkyl radical, an optionally substituted aryl radical, an optionally substituted aralkyl radical, a monohydroxyalkyl or polyhydroxyalkyl radical or a lower acyl radical,
R$_{13}$ represents a lower alkyl radical, a radical OR$_{15}$ or a radical

R$_{15}$, R' and R" having the meanings given below,
R$_{14}$ and R$_{15}$ which may be identical or different, represent a hydrogen atom, a lower alkyl radical, an aryl radical, an optionally substituted aralkyl radical, a monohydroxyalkyl radical or a polyhydroxyalkyl radical,
R' and R", which may be identical or different, represent a hydrogen atom, a lower alkyl radical, a mono- or polyhydroxyalkyl radical, an optionally substituted aryl radical or an amino acid residue, or alternatively, taken together with the nitrogen atom, form a heterocycle,
as well as the salts thereof and the optical and geometrical isomers thereof.

2. The compounds according to claim 1, which are in the form of salts of an alkali metal or alkaline earth metal, or alternatively of zinc or of an organic amine.

3. The compounds according to claim 1, wherein the lower alkyl radicals comprise methyl, ethyl, isopropyl, butyl or tert-butyl radicals.

4. The compounds according to claim 1, wherein the monohydroxyalkyl radicals comprise 2-hydroxyethyl, 2-hydroxypropyl and 3-hydroxypropyl radicals.

5. The compounds according to claim 1, wherein the polyhydroxyalkyl radicals comprise 2,3-dihydroxypropyl, 2,3,4-trihydroxybutyl and 2,3,4,5-tetrahydroxypentyl radicals or a pentaerythritol residue.

6. The compounds according to claim 1, wherein the aryl radical is a phenyl radical optionally substituted with at least one halogen atom, a hydroxyl radical or a nitro function.

7. The compounds according to claim 1, wherein the aralkyl radicals comprise benzyl or phenethyl radicals, optionally substituted with at least one halogen atom, a hydroxyl or a nitro fuinction.

8. The compounds according to claim 1, wherein the amino acid residues comprise residues derived from one of the 20 amino acids of L or D configuration which constitute mammalian proteins.

9. The compounds according to claim 1, wherein the heterocyclic radicals comprise piperidino, morpholino, pyrrolidino or piperazino radicals, optionally substituted in position 4 with a C$_1$–C$_6$ alkyl or mono- or polyhydroxyalkyl radical.

10. The compounds according to claim 1, wherein the polyether radicals comprise methoxymethyl ether, methoxyethoxymethyl ether or methylthiomethyl ether radicals.

11. The compounds according to claim 1, which are selected, alone or as mixtures, from:
   Ethyl 3-methyl-5-(5,5,8,8-tetramethyl-5,6,7,8-tetrahydronaphthaten-2-ylselenyl)pent-2-en-4-ynoate
   3-Methyl-5-(5,5,8,8-tetramethyl-5,6,7,8-tetrahydronaphthalen-2-ylselenyl)pent-2-en-4-ynoic acid
   Ethyl 3-methyl-5-(3,5,5,8,8-pentamethyl-5,6,7,8-tetrahydronaphthalen-2-ylselenyl)pent-2-en-4-ynoate
   3-Methyl-5-(3,5,5,8,8-pentanethyl-5,6,7,8-tetrahydronaphthalen-2-ylselenyl)pent-2-en-4-ynoic acid
   Ethyl 3-methyl-5-(5,5,8,8-tetramethyl-5,6,7,8-tetahydronaphthalen-2-ylsulphonyl)pent-2-en-4-ynoate
   3-Methyl-5-(5,5,8,8-tetramethyl-5,6,7,8-tetrahydronaphthalen-2-ylsulphonyl)pent-2-en-4-ynoic acid
   Ethyl 3-methyl-5-(3,5,5,8,8-pentamethyl-5,6,7,8-tetrahydronaphthalen-2-ylsulphonyl)pent-2-en-4-ynoate
   3-Methyl-5-(3,5,5,8,8-pentamethyl-5,6,7,8-tetrahydronaphthalen-2-ylsulphonyl)pent-2-en-4-ynoic acid
   Ethyl 3-methyl-5-(5,5,8,8-tetramethyl-3-propoxy-5,6,7,8-tetrahydronaphthalen-2-ylselenyl)pent-2-en-4-ynoate
   3-Methyl-5-(5,5,8,8-tetramethyl-3-propoxy-5,6,7,8-tetrahydronaphthalen-2-ylselenyl)pent-2-en-4-ynoic acid
   Ethyl 3-methyl-5-(5,5,8,8-tetramethyl-4-propoxy-5,6,7,8-tetrahydronaphthalen-2-ylselenyl)pent-2-en-4-ynoate
   3-Methyl-5-(5,5,8,8-tetramethyl-4-propoxy-5,6,7,8-tetrahydronaphthalen-2-ylselenyl)pent-2-en-4-ynoic acid
   Ethyl 5-(4-methoxymethoxy-5,5,8,8-tetramethyl-5,6,7,8-tetrahydronaphthalen-2-ylselenyl)-3-methylpent-2-en-4-ynoate
   5-(4-Methoxymethoxy-5,5,8,8-tetramethyl-5,6,7,8-tetrahydronaphthalen-2-ylselenyl)-3-methylpent-2-en-4-ynoic acid Ethyl 5-(3-hydroxy-5,5,8,8-tetramethyl-5,6,7,8-tetrahydronaphthalen-2-ylselenyl)-3-methylpent-2-en-4-ynoate 5-(3,5,5,8,8-Pentamethyl-5,6,7,8-tetrahydro-naphthalen-2-ylselenyl)-3-phenylpent-2-en-4-ynoic acid 5-(4-Methoxymethoxy-5,5,8,8-tetramethyl-5,6,7,8-tetrahydronaphthalen-2-ylselenyl)-3-phenylpent-2-en-4-ynoic acid Methyl 5-(4-hydroxy-5,5,8,8-tetramethyl-5,6,7,8-tetrahydronaphthalen-2-ylselenyl)-3-phenylpent-2-en-4-ynoate 3-Propyl-5-(5,5,8,8-tetramethyl-5,6,7,8-tetrahydronaphthalen-2-ylselenyl)pent-2-en-4-ynoic acid 5-(4-Benzyloxy-3-bromo-5,5,8,8-tetramethyl-5,6,7,8-tetrahydronaphthalen-2-ylselenyl)-3-methylpent-2-en-4-ynoic acid 5-(4-Benzyloxy-5,5,8,8-tetramethyl-5,6,7,8-tetrahydronaphthalen-2-ylselenyl)-3-phenylpent-2-en-4-ynoic acid Ethyl 5-[5-adamantan-1-yl-4-(2-methoxyethoxymethoxy)-2-methylphenylselenyl]-3-methylpent-2-en-4-ynoate 5-[5-Adamantan-1-yl-4-(2-methoxyethoxymethoxy)-2-methylphenylselenyl]-3-methylpent-2-en-4-ynoic acid 5-[5-Adamantan-1-yl-4-(2-methoxyethoxymethoxy)-2-methylphenylselenyl]-3-propylpent-2-en-4-ynoic acid 5-[5-Adamantan-1-yl-4-(2-methoxyethoxymethoxy)-2-methylphenylselenyl]-3-phenylpent-2-en-4-ynoic acid Ethyl5-(3,5-di-tert-butyl-2-methoxymethoxyphenylselenyl)-3-methylpent-2-en-4-ynoate 5-(3,5-Di-tert-butyl-2-methoxymethoxyphenyl-selenyl)-3-methylpent-2-en-4-ynoic acid Ethyl 3-methyl-5-(5,5,8,8-tetramethyl-3-hexyloxy-5,6,7,8-tetrahydronaphthalen-2-ylselenyl)pent-2-en-4-ynoate 3-Methyl-5-(5,5,8,8-tetramethyl-3-hexyloxy-5,6,7,8-tetrahydronaphthalen-2-ylselenyl)pent-2-en-4-ynoic acid 5-[4-Adamantan-1-yl-3-(2-methoxyethoxymethoxy)-phenylselenyl]-3-propylpent-2-en-4-ynoic acid Ethyl 5-[2-(adamantan-1-yl)-1-methoxyethoxymethoxyphen-5-ylselenyl)-3-methylpent-2-en-4-ynoate Ethyl5-[4-(2-methoxyethoxymethoxy)-5,5,8,8-tetramethyl-5,6,7,8-tetrahydronaphthalen-2-ylsulphonyl]-3-methylpent-2-en-4-ynoate (Z)-5-[4-(2-Methoxyethoxymethoxy)-5,5,8,8-tetramethyl-5,6,7,8-tetrahydronaphthalen-2-ylsulphonyl]-3-methylpent-2-en-4-ynoic acid (E)-5-[4-(2-Methoxyethoxymethoxy)-5,5,8,8-tetramethyl-5,6,7,8-tetrahydronaphthalen-2-ylsulphonyl]-3-methylpent-2-en-4-ynoic acid Methyl 5-(3,5,5,8,8-pentamethyl-5,6,7,8-tetrahydronaphthalen-2-ylsulphonyl)penta-2,4-diynoate Ethyl 5-(3-benzyloxy-5,5,8,8-tetramethyl-5,6,7,8-tetrahydronaphthalen-2-ylselenyl)-3-methylpent-2-en-4-ynoate 5-(3-Benzyloxy-5,5,8,8-tetramethyl-5,6,7,8-tetrahydronaphthalen-2-ylselenyl)-3-methylpent-2-en-4-ynoic acid Ethyl5-[3-(2-methoxyethoxymethoxy)-5,5,8,8-tetramethyl-5,6,7,8-tetrahydronaphthalen-2-ylselenyl]-3-methylpent-2-en-4-ynoate 5-[3-(2-Methoxyethoxymethoxy)-5,5,8,8-tetra-methyl-5,6,7,8-tetrahydronaphthalen-2-ylselenyl]-3-methylpent-2-en-4-ynoic acid Methyl 5-(3,5,5,8,8-pentamethyl-5,6,7,8-tetrahydronaphthalen-2-ylselenyl)penta-2,4-diynoate Ethyl 5-(4-benzyloxy-5,5,8,8-tetramethyl-5,6,7,8-tetrahydronaphthalen-2-ylselenyl)-3-methylpent-2-en-4-ynoate Ethyl 5-[3-[5-(tert-butyldimethylsilanyloxy)-pentyloxymethyl]-5,5,8,8-tetramethyl-5,6,7,8-tetrahydronaphthalen-2-ylselenyl]-3-methylpent-2-en-4-ynoate 5-[3-[5-(tert-Butyldimethylsilanyloxy)pentyloxymethyl]-5,5,8,8-tetramethyl-5,6,7,8-tetrahydronaphthalen-2-ylselenyl]-3-methylpent-2-en-4-ynoic acid Ethyl 5-[3-(5-hydroxypentyloxy)-5,5,8,8-tetra-methyl-5,6,7,8-tetrahydronaphthalen-2-ylselenyl]-3-methylpent-2-en-4-ynoate or 5-(6-Bromo-4,4-dimethylthiochroman-8-ylselenyl)-3-methylpent-2-en-4-ynoic acid.

12. The compounds according to claim 1, which have at least one of the following characteristics:

$R_1$ represents a radical —$COR_6$;

X represents an Se or S radical;

the group —X—Y—$R_1$ is in the para position relative to the substituent $R_3$ on the aromatic ring;

$R_2$ and $R_3$, taken together, form, with the adjacent aromatic ring, a 5- or 6-membered ring optionally substituted with methyl groups and/or optionally interrupted by an oxygen or sulphur atom, or $R_2$ or $R_3$ is a 1-adamantyl radical.

13. A pharmaceutical composition comprising, in a pharmaceutically acceptable support, an effective amount of at least one of the compounds as defined in claim 1.

14. The composition according to claim 13, wherein the concentration of compound(s) is between 0.001% and 5% by weight relative to the whole composition.

15. A cosmetic composition comprising, in a cosmetically acceptable support, an effective amount of at least one of the compounds as defined in claim 1.

16. The composition according to claim 15, wherein the concentration of compound(s) according to claim 1 is between 0.001% and 3% by weight relative to the whole composition.

* * * * *